US010656156B2

(12) United States Patent
Ravindranath et al.

(10) Patent No.: US 10,656,156 B2
(45) Date of Patent: May 19, 2020

(54) DIAGNOSTIC AND THERAPEUTIC POTENTIAL OF HLA-E MONOSPECIFIC MONOCLONAL IGG ANTIBODIES DIRECTED AGAINST TUMOR CELL SURFACE AND SOLUBLE HLA-E

(75) Inventors: Mepur H. Ravindranath, Los Angeles, CA (US); Paul I. Terasaki, Los Angeles, CA (US)

(73) Assignee: Mepur Ravindranath, Los Angeles, CA (US)

( * ) Notice: Subject to any disclaimer, the term of this patent is extended or adjusted under 35 U.S.C. 154(b) by 853 days.

(21) Appl. No.: 13/507,537

(22) Filed: Jul. 5, 2012

(65) Prior Publication Data

US 2014/0010825 A1  Jan. 9, 2014

(51) Int. Cl.
| A61K 39/00 | (2006.01) |
| C07K 16/28 | (2006.01) |
| G01N 33/574 | (2006.01) |

(52) U.S. Cl.
CPC ... *G01N 33/57492* (2013.01); *C07K 16/2833* (2013.01); *C07K 2317/33* (2013.01); *C07K 2317/34* (2013.01); *C07K 2317/74* (2013.01); *C07K 2317/76* (2013.01); *G01N 2333/70539* (2013.01)

(58) Field of Classification Search
None
See application file for complete search history.

(56) References Cited

U.S. PATENT DOCUMENTS

| 4,816,397 | A | 3/1989 | Boss et al. |
| 4,816,567 | A | 3/1989 | Cabilly et al. |
| 5,225,539 | A | 7/1993 | Winter |
| 5,413,923 | A | 5/1995 | Kucherlapati et al. |
| 5,530,101 | A | 6/1996 | Queen et al. |
| 5,545,806 | A | 8/1996 | Lonberg et al. |
| 5,565,332 | A | 10/1996 | Hoogenboom et al. |
| 5,569,825 | A | 10/1996 | Lonberg et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,766,886 | A | 6/1998 | Studnicka et al. |
| 5,807,715 | A | 9/1998 | Morrison et al. |
| 5,814,318 | A | 9/1998 | Lonberg et al. |
| 5,939,598 | A | 8/1999 | Kucherlapati et al. |
| 6,331,415 | B1 | 12/2001 | Cabilly et al. |
| 6,407,213 | B1 | 6/2002 | Carter et al. |
| 9,056,911 | B2 * | 6/2015 | Yang ............... C07K 16/3007 |
| 2003/0125247 | A1 | 7/2003 | Rosen et al. |
| 2003/0171267 | A1 | 9/2003 | Rosen et al. |
| 2003/0199043 | A1 | 10/2003 | Ballance et al. |
| 2003/0219875 | A1 | 11/2003 | Rosen et al. |
| 2004/0010134 | A1 | 1/2004 | Rosen et al. |
| 2004/0171123 | A1 | 9/2004 | Rosen et al. |
| 2005/0042664 | A1 | 2/2005 | Wu et al. |

FOREIGN PATENT DOCUMENTS

| EP | 0 239 400 A2 | 9/1987 |
| EP | 0 413 622 A1 | 2/1991 |
| EP | 0 519 596 A1 | 12/1992 |
| EP | 0 592 106 A1 | 4/1994 |
| WO | WO 91/09967 A1 | 7/1991 |
| WO | WO 93/15199 A1 | 8/1993 |
| WO | WO 93/15200 A1 | 8/1993 |
| WO | WO 93/17105 A1 | 9/1993 |
| WO | WO 96/33735 A1 | 10/1996 |
| WO | WO 96/34096 A1 | 10/1996 |
| WO | WO 98/24893 A2 | 6/1998 |
| WO | WO 06/063844 A1 | 6/2006 |
| WO | WO 09/023055 A2 | 2/2009 |

OTHER PUBLICATIONS

Murray et al (J. Chromat. Sci. 2002, 40(6): 343-3491).*
Papassavas et al (Human Immunol., 2000, 61(7): 705-710).*
Yari et al (Hybridoma and Hybridomics, 2003, 22(5): 301-308).*
de Kruijf et al (J. Immunol. 2020, 185: 7452-7459).*
Kaiser et al (PNAS, 2008, 105(18): 6696-6701).*
Uniprot Q9TQMO, 2000.*
UniProtKB-P113747 (Nov. 2016).*
Hancock and O'Reilly (Methods in Mol. Biol., 2005, vol. 295, Ed. R. Burns, Human Press, Inc., Totowa, NJ, section 1.1.3 on p. 17).*
Sasaki et al (Int. J. Canc., 2013, 134: 1558-1570).*
Miller et al (J. Immunol. 2003, 171: 1369-1375).*
Anderson et al (1986, J. Clin. Microbiol. 23: 475-480) (Year: 1986).*
Shi et al (2006, J. Immunol. Meth. 314: 9-20) (Year: 2006).*
Edwards et al (JMB, 2003, 334: 103-118) (Year: 2003).*
Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*

(Continued)

*Primary Examiner* — G. R. Ewoldt
*Assistant Examiner* — Marianne DiBrino
(74) *Attorney, Agent, or Firm* — Squire Patton Boggs (US) LLP

(57) ABSTRACT

Provided herein are compositions comprising purified antibodies and fragments thereof that are specifically immunoreactive to only human leukocyte antigen E (HLA-E) but not to other HLA Ia and HLA-Ib alleles. Also provided are methods of their making and diagnostic and therapeutic applications. The monospecific HLA-E antibodies are highly specific and can be used for diagnosing or localizing the presence of HLA-E on normal or diseased cells or tissues. The monospecific HLA-E antibodies can also be used for cancer therapies, likely through regulation of the CD94/NKG2a on Cytotoxic and/or Natural Killer T cells.

7 Claims, 13 Drawing Sheets
Specification includes a Sequence Listing.

(56) References Cited

OTHER PUBLICATIONS

Torres and Casadevall (Trend. Immunol., 2008, 29(2): 91-97) (Year: 2008).*
Berger et al (Int. J. Cancer. 111: 229-237, 2004) (Year: 2004).*
Kalos and Jun. (Immunity, 2013, 39: 49-60) (Year: 2013).*
Spranger, S (Int. Immunol. 2015, 28(8): 383-391) (Year: 2015).*
Beatty and Gladney (Clin. Canc. Res. 2014, 21(4): 687-692) (Year: 2014).*
Kerkar and Restifo (Cancer Res. 2012, 72(13): 3125-3130) (Year: 2012).*
Vitale et al (Eur. J. Immunol. 2014, 44: 1582-1592) (Year: 2014).*
International Search Report for PCT/US2011/068178, dated Jun. 22, 2012, 14 pgs.
Written Opinion for PCT/US2011/068178, dated Jan. 15, 2013, 8 pgs.
Coupel et al., "Expression and release of soluble HLA-E is an immunoregulatory feature of endothelial cell activation", Blood (2007) 109:2806-2814 (2007).
Kren et al., "Production of immune-modulatory nonclassical molecules HLA-G and HLA-E by tumor infiltrating ameboid microglia/macrophages in glioblastomas: a role in innate immunity?", J. of Neuroimmunology (2010) 220:131-135.
Lo Monaco et al.,"HLA-E and the origin of immunogenic self HLA epitopes", Molecular Immunology (2010) 47:1661-1662.
Menier et al., "Characterization of Monoclonal Antibodies Recognizing HLA-G or HLA-E: New Tools to Analyze the Expression of Nonclassical HLA Class I Molecules", Human Immunology (2003) 64:315-326.
Pacasova et al., "Cell surface detection of HLA-E gene products with a specific monoclonal antibody", J. of Reproductive Immunology (1999) 43:195-201.
Ravindranath et al., "HLA-E monoclonal antibody MEM-E/02 binds to discontinuous but shared peptide sequences on HLA B&C heavy chains not treated by acid", Molecular Immunology (2010) 47:1663-1664.
Ravindtranath et al., "Anti HLA-E mAb 3D12 mimics MEM-E/02 in binding to HLA-B and HLA-C alleles: Web-tools validate the immunogenic epitopes of HLA-E recognized by the antibodies", Molecular Immunology (2011) 48:423-430.
Ravindtranath et al., "Antibodies to HLA-E in Nonalloimmunized Males: Pattern of HLA-Ia Reactivity of Anti-HLA-E-Positive Sera", J. of Immunol. (2010) 185:1935-1948.
Ravindtranath et al., "HLA-E monoclonal antibodies recognize shared peptide sequences on classical HLA class Ia: Relevance to human natural HLA natibodies", Molecular Immunology (2010) 47:1121-1131.
Seitz et al., "The monoclonal antibody HCA2 recognises a broadly shared epitope on selected classical as well as several non-classical HLA class I molecules", Molecular Immunology (1998) 35:819-827.
Sibilio et al., "Biochemical characterization of monoclonal antibodies to HLA-E and HLA-G", Tissue Antigens (2003) 62:273-357, Abstract only.
Sullivan et al., "The major histocompatibility complex class Ib molecule HLA-E at the interface between innate and adaptive immunity", Tissue Antigens (2008) 72:415-424.
Wischhusen et al., "Immune-refractory cancers and their little helpers—An extended role for immunetolerogenic MHC molecules HLA-G and HLA-E?", Seminars in Cancer Biology (2007) 17:459-468.
International Search Report and Written Opinion, dated Dec. 5, 2013, in PCT/US2013/048975, 10 pages.
Agaugué et al., Human natural killer cells exposed to IL-2, IL-12, IL-18, or IL-4 differently modulate priming of naive T cells by monocyte-derived dendritic calls (2008) Blood 112:1776-1783.
Bahri et al., Soluble HLA-G Inhibits Cell Cycle Progression in Human Alloreactive T Lymphocytes (2006) The Journal of Immunology 176:1331-1339.
Braud et al., HLA-E binds to natural killer cell receptors CD94/NKG2A, B and C (1998) Nature 391:795-799.
Lo Monaco et al., HLA-E: Strong Association with $\beta_2$-Microglobulin and Surface Expression in the Absence of HLA Class I Signal Sequence-Derived Peptides (2008) The Journal of Immunology 181:5442-5450.
Pietra et al., The Emerging Role of HLA-E-Restricted CD8+ T Lymphocytes in the Adaptive Immune Response to Pathogens and Tumors (2010) Journal of Biomedicine and Biotechnology 10:1-8.
Rouas-Freiss et al., The immunotolerance role of HLA-G (1999) Seminars in Cancer Biology (1999) 9:3-12.
Ravindranath et al., Anti-HLA-E Monoclonal Antibodies Reacting with HLA-Ia and Ib Alleles Like IVIg as Potential IVIg-Immunomimetics: An Evolving Therapeutic Concept (2013) Clinical Transplants, Chapter 35:293-305.
Zhu et al., Suppression of allo-human leucocyte antigen (HLA) antibodies secreted by B memory cells in vitro: intravenous immunoglobulin (IVIg) versus a monoclonal anti-HLA-E IgG that mimics HLA-I reactivities of IVIg (2014) Clinical and Experimental Immunology, pp. 1-14.
Ravindranath et al., Suppression of Blastogenesis and Proliferation of activated CD4+ T-cells: IVIg versus novel anti-HLA-E mAbs mimicking HLA-I reactivity of IVIg. Clin Exp Immunol. Jun. 2, 2014. doi: 10.1111/cei.12391. [Epub ahead of print] pp. 1-69.
Crow et al., The neonatal Fc receptor (FcRn) is not required for IVIg or anti-CD44 monoclonal antibody—mediated amelioration of murine immune thrombocytopenia (2011) Blood 118:6403-6406.
HLA Alleles Numbers, HLA Nomenclature, http://hla.alieles.org/nomenclature.stats.html, printed Mar. 17, 2015, pp. 1-2.
International Search Report and Written Opinion for PCT/US2013/021054, dated Jul. 18, 2013, 10 pages.
Mouthon et al., Mechanisms of action of intravenous immune globulin in immune-mediated disease (1996) Clin. Exp. Immunol. 104:Suppl 1, abstract at pp. 1-2.
Ravindranath et al., Augmentation of anti-HLA-E antibodies with concomitant HLA-Ia reactivity in IFNγ-treated autologous melanoma cell vaccine recipients (2012) Journal of Immunotoxicology 9:282-291.
Yu et al., Mechanism of Intravenous Immune Globulin Therapy in Antibody-Mediated Autoimmune Diseases (1999) Blood 340:227-228.
Ravindranath, Mepur H., et al., "The Monospecificity of Novel Anti-HLA-E Monoclonal Antibodies Enables Reliable Immunodiagnosis, Immunomodulation of HLA-E, and Upregulation of CD8+ T Lymphocytes" (2015) Monoclonal Antibodies in Immunodiagnosis and Immunotherapy 34(3):135-153.
Ravindranath, Mepur H., et al., "HLA-E restricted monoclonal antibodies: Therapeutic potential as a double-edged sword against tumor progression" (2017) Internal Medicine Review 3(12):1-49.

* cited by examiner

| HLA Class I | Peptide [# 1] specific for HLA-E ||||||||||
| | α1 | α1 | α1 | α1 | α1 | α1 | α1 | α1 | α1 |
| | 65 | 66 | 67 | 68 | 69 | 70 | 71 | 72 | 73 |
| E*01010101 | R | S | A | R | D | T | A | Q | I |
| G*01010101 | R | N | T | K | A | H | A | Q | T |
| F*01010101 | G | Y | A | K | A | N | A | Q | T |

| HLA Class I | Peptide [# 3] specific for HLA-E ||||||||||||||||||||
| | α2 | α2 | α2 | α2 | α2 | α2 | α2 | α2 | α2 | α2 | α2 | α2 | α2 | α2 | α2 | α2 | α2 | α2 | α2 | α2 |
| | 143 | 144 | 145 | 146 | 147 | 148 | 149 | 150 | 151 | 152 | 153 | 154 | 155 | 156 | 157 | 158 | 159 | 160 | 161 | 162 |
| E*01010101 | S | E | G | K | S | N | D | A | S | E | A | E | H | Q | R | A | Y | L | E | D |
| G*01010101 | S | K | R | K | C | E | A | A | N | V | A | E | Q | R | R | A | Y | L | E | G |
| F*01010101 | T | Q | R | F | Y | E | A | E | E | Y | A | E | E | F | R | T | Y | L | E | G |

Figure 1A

DIAGNOSTIC AND THERAPEUTIC POTENTIAL OF HLA-E MONOSPECIFIC MONOCLONAL IGG ANTIBODIES DIRECTED AGAINST TUMOR CELL SURFACE AND SOLUBLE HLA-E

1. FIELD OF THE INVENTION

Provided herein are monospecific HLA-E antibodies and fragments thereof that have no reactivity to other human leukocyte antigen (HLA) class I antigens except those presented by HLA-E (hereinafter referred to as "monospecific HLA-E antibodies" or "monospecific anti-HLA-E" or "monospecific anti-HLA-E antibodies"). Also provided herein are methods for generating the same as well as diagnostic and therapeutic applications using compositions comprising the same. Here, HLA-E can be expressed as heavy chain or heavy chain in combination with β2 microglobulin (β2m), for example, on the cell surface of various inflammatory and human cancer tissues. The monospecific HLA-E antibodies are also reactive to antigens presented by soluble HLA heavy chain or heavy chain-β2m combination in circulation or tumor microenvironment.

2. BACKGROUND

Major histocompatibility complex (MHC) class I molecules include highly polymorphic classical HLA class Ia (HLA-A: 1729 alleles with 1,264 proteins; HLA-B: 2329 alleles, 1786 proteins; and HLA-Cw: 1291 alleles, 938 proteins) and least polymorphic non-classical HLA-Ib (HLA-E: 10 alleles, 3 proteins; HLA-F: 22 alleles, 4 proteins; and HLA-G: 47 alleles, 15 proteins), based on information published in October 2011 in EBML-EBI website at www<dot>ebi<dot>ac<dot>uk</>imgt</>hla</>stats<dot>html.

Each HLA molecule consists of a heavy chain (HC) of about 346 amino acids in length. An HC consists of three extracellular domains (α1, α2 & α3), a transmembrane domain and a C-terminal cytoplasmic domain. In some cases, the HC is non-covalently linked to β2-microglobulin ("β2 m"), which is about 99 amino acids in length.

HLA-E was first discovered in 1987; see, for example, Geraghty et al., 1987, Proc. Natl. Acad. Sci. U.S.A. 84: 9145-9149; and Koller et al., 1988, J. Immunol. 141: 897-904. One of the functions of HLA-E is to present peptides to CD8+ T-lymphocytes. The peptides presented include but are not limited to (1) All leader sequence peptides of HLA-Ia antigens, namely HLA-A, HLA-B and HLA-Cw and (2) peptides from (a) Heat Shock Proteins (Hsp-60), (b) cytomegalovirus (CMV), (c) Epstein Barr Virus (EBV); (d) Influenza virus, (e) *Salmonella* enteric and (f) *Mycobaterium* glycoproteins (Iwaszko and Bogunia-Kubik, 2011 *Arch Immunol Ther Exp.* 59(5):353-367).

The HLA-E gene is expressed in resting T-lymphocytes. It is also commonly expressed by cells such as endothelial cells, immune cells (B-, T-lymphocytes, NK cells, monocytes and macrophages), and trophoblasts. Most importantly, HLA-E is overexpressed in tumor cells, possibly caused by malignant transformation of human tissues. See, for example, Marin R et al., 2003 Immunogenetics. 54:767-775; Wischhusen J et al., 2005, J Neuropathol Exp Neurol. 64:523-528; Derré L et al., 2006. J. Immunol. 177:3100-3107; Mittelbronn et al., 2007 J. Neuroimmunol. 189: 50-58; Goncalves et al. 2008, Stangl et al., 2008, Cell Stress Chaperones 13(2):221-230; Levy et al., 2009, Innate Immun. 15(2):91-100; Hanak L et al., 2009, Med Sci Monit. 15(12):CR638-643; Sensi M, et al., 2009, Int Immunol. 21(3):257-268; de Kruijf E M et al., 2010 J. Immunol. 185:7452-7459; Kren L et al., 2010 J. Neuroimmunol. 220:131-135; Kren L et al., 2011 Neuropathology 31:129-134; Kren L et al., 2012 Diagnostic Pathology 7:58; Kren L, et al., 2012 Pathology: Research and Practice 208: 45-49; Allard M et al., 2011 PLoS One. 6(6):e21118; Benevolo M, et al., 2011, J Transl Med. 9:184; Gooden M et al., 2011, Proc Natl Acad Sci USA. 108:10656-10661; and Silva T G et al., 2011, Histol Histopathol. 26:1487-1497; each of which is hereby incorporated by reference herein in its entirety.

Increased cellular expression of HLA-E induces the release of HLA-E in circulation (e.g., Derré L et al., 2006. J. Immunol. 177:3100-3107). For example, soluble HLA-E (sHLA-E) is found in the sera or plasma of patients with immune-mediated vascular diseases, Kawasaki Disease, a systemic pediatric vasculitis, as well as in normal individuals (e.g., Lin et al., 2009 Arthritis & Rheumatism 60(2): 604-610).

The soluble HLA-E (sHLA-E) may be found without β2m. In intact HLA-E, the presence of β2m can mask some of the peptides sequences of the sHLA-E heavy chain that would be otherwise exposed and become immunogenic. In other words, some of the peptide sequences of sHLA-E have lost immunogenic capacity due to association with β2m.

Several monoclonal antibodies to HLA-E are available commercially. They include MEM-E/02, MEM-E/06, MEM-E/07, MEM-E/08, mAb 3D12 and mAb DT9. These anti-HLA-E monoclonal antibodies were used for cancer diagnosis based on their assumed specificity for HLA-E. See, for example, Shimizu et al., 1988, Proc Natl Acad Sci USA. 85:227-231; Menier et al., 2003, Hum Immunol. 64(3):315-326; Gooden M et al., 2011, Proc Natl Acad Sci USA. 108:10656-10661; Stangl et al., 2008, Cell Stress Chaperones 13(2):221-230; Allard M et al., 2011 PLoS One. 6(6):e21118; Levy et al., 2009, Innate Immun. 15(2):91-100; and Sensi M, et al., 2009, Int Immunol. 21(3):257-268; each of which is hereby incorporated by reference herein in its entirety.

These known anti-HLA-E monoclonal antibodies, however, have been shown to cross-react with other antigens. For example, Ravindranath et al. showed that MEM-E/02 antibodies bind A*2402, B*1301, B*1401, B*1502, B*1513, B*1801, B*3501, B*3701, B*4001, B*4006, B*4101, B*4403, B*4501, B*4601, B*5601, B*7301, B*7801, B*8201, Cw*0102, Cw*0304, Cw*0501, Cw*0602, Cw*0701, Cw*1802 at 1/300 dilution. In the same study, MEM-E/06 antibodies were shown to bind B*1401, B*4006, B*4101, B*8201, Cw*0501, Cw*0802, Cw*0701, Cw*1802 at 1/300 dilution. MEM-E/07 and E/08 also antibodies were to bind B*1301, B*3801, B*4006, B*4101 (E/07 only), B*8201 (E/07 only), Cw*0501, Cw*0701, Cw*1802 at 1/300 dilution. MEM-E/07 and MEM-E/08 were shown to react reasonably well with HLA-G. In addition, an anti-HLA-E murine mAb 3D12 also reacted with several HLA Class Ia alleles. See, for example, Ravindranath et al., 2010, Mol. Immunol. 47: 1121-1131 and Ravindranath et al., 2010, Mol. Immunol. 47.1663-1664. Further, it was reported that yet another anti-HLA-E mAb, mAb DT9 strongly reacted with HLA-A*8001, N*1301, B*3501, B*4006 and B*7301. See, e.g., Shimizu et al., 1988, Proc Natl Acad Sci USA. 85:227-231; which is hereby incorporated by reference herein in its entirety.

The cross reactivity of anti-HLA-E mAbs to HLA-A, -B or -Cw is possibly due to recognition of shared epitopes found between HLA-E and HLA-Ia alleles (Table 1). See, Ravindranath et al., 2010, Mol. Immunol. 47. 1663-1664; and Ravindranath et al., 2010, J. Immunol. 185: 1935-1948.

CD94 and NKG2a receptors are present on CD8+ T lymphocytes and Natural Killer T Cells. When an HLA-E binds to CD94 and NKG2a receptors on CD8+ T cells and NKT cells, incoming activation signals of T cells are dampened by recruitment of phosphatases like SHP-1 to the signal transducing synapse, which results in decreased effector functions (e.g., Rodgers and Cook, 2005, Nat Rev Immunol 5:459; Chang W C et al., 2005, Int J Gynecol Cancer 15:1073; and Lanier L L, 2005, Annu Rev Immunol 23:225). In other words, in the absence of activating signals, the CD8+ cells remain paralyzed, unless the proliferation of activated CD8+ T cells are augmented to exceed interaction with HLA-E expressing cells.

In contrast to overexpression of HLA-E, loss of MHC class Ia expression is known to occur in several cancers including primary and metastatic melanoma. Thus, loss of MHC class Ia expression and increased CD94/NKG2-A/B expression are linked with tumor progression (Vetter et al., 2000 J. Invest. Dermatol. 114: 941-947).

In general, the events taking place in the tumor microenvironment can be summarized as follows: CD8+ Cytotoxic T cells (CTLs) and NKT cells infiltrate tumor tissue to destroy tumor cells. CD8+ CTLs release IFN-γ after infiltrating into tumor cells. IFN-γ induces overexpression of HLA-E. HLA-E epitopes functions as a major ligand for CD8+ Cytotoxic Lymphocytes (CTL) and the Natural Killer T cell (NKT) inhibitory receptor CD94/NKG2A (FIGS. 1A and 1B). CD8+ T cells with CD94/NKG2A are more in tumor tissues than in peripheral blood. Both overexpression of CD94, NKG2a & HLA-E may vary with the stages of cancer, from primary to lymph node & organ metastasis.

Survival curves in ovarian cancer have been compared in relation to the expression of HLA-E in tumor and CD8+ on T cells (Gooden M et al 2011. Proc. Natl. Acad. Sci. U.S.A. 108(26):10656-10661). Patients with high levels of tumor infiltrating CD8+ T cells survive significantly ($p<0.04$) higher than those with low CD8+ T cells. The survival of patients is significantly ($p<0.001$) higher when high CD8+ T cells co-exist with tumor cells with low level of expression of HLA-E. However, the survival of patients with high CD8+ T cells are much lowered to the level of low CD8 T cells.

One of the salient strategies to overcome HLA-E-mediated inactivation of CTLs/NKTs is to block HLA-E on the tumor cell surface with antibodies designed to block only and specifically HLA-E. These antibodies have the potential to prevent with the ligand-receptor interaction between tumor cells expressing HLA-E and CD94 and NKG2a receptors on CD8+ T cells and NKT cells.

Whether HLA-E blocking HLA-E specific monoclonal antibodies are capable of any other immunomodulatory functions deserves to be elucidated before chimeric or humanized monoclonal antibodies are introduced into the patients.

What is needed are truly monospecific antibodies that that have no reactivity to other human leukocyte antigen (HLA) class I antigens except HLA-E. Such monospecific antibodies would be more reliable and invaluable for immunodiagnosis of HLA-E in normal and pathological tissue samples overexpressing HLA-E.

3. SUMMARY

In one aspect, the provided herein are "monospecific HLA-E antibodies" or "monospecific anti-HLA-E" and methods for generating the same. In certain embodiments, the monospecific HLA-E antibodies provided herein are chimeric, humanized or human antibodies. Also provided herein are compositions comprising the monospecific HLA-E antibodies that are chimeric, humanized or human antibodies.

Exemplary monospecific HLA-E monoclonal antibodies are listed in Table 3. Two alleles of HLA-E are used for immunization: HLA-E$^{R107}$ and HLA-E$^{G107}$. PTER designates clones generated with the HLA-E$^{R107}$ allele while PTEG designates clones generated with the HLA-E$^{G107}$ allele. Also provided herein are affinities of HLA-E monospecific monoclonal antibodies for HLA-E at different purification steps (culture supernatant, protein-G purification, concentration after Protein G purification), at varying dilutions of the concentrated mAbs (e.g., FIGS. 2 & 3) developed for the specific diagnosis of HLA-E overexpression in tumor biopsies, cell lines and non-malignant inflamed tissues and for immunomodulatory therapy for human cancers. The monospecificity of mAbs (e.g. PTER-033) is confirmed by dose-dependent peptide inhibition using two of the HLA-E monospecific peptide epitopes listed in Table 2 (e.g., FIG. 4). p In certain embodiments, the pharmaceutical compositions are uniform in composition and can be minimized by clearing soluble HLA-E either present in tumor microenvironment or in circulation or blood (plasma or serum), synovial fluid, seminal fluid or in any other body fluid, in order to block anti-tumor efficacious HLA-E ligand binding to CD94and NKg2a cytotoxic inhibitory receptors located on tumor infiltrating and circulatory cytotoxic CD8+ T lymphocytes and NKG2a cells (e.g., FIGS. 1A and 1B).

Certain pharmaceutical compositions provided herein comprise these anti-HLA-E monospecific monoclonal antibodies in a pharmaceutically acceptable carrier, wherein said antibodies are chimeric, humanized or human anti-HLA-E monospecific monoclonal antibodies immunoreactive to HLA-E and not immunoreactive to other HLA-Ia (HLA-A/-B/-Cw) and HLA-Ib (HLA-F/-G) molecules.

In some embodiments, the anti-HLA-E monospecific antibodies are purified monoclonal antibodies, a mixture of two or more types of purified monospecific antibodies, recombinantly produced antibodies, Fab fragments, F(ab') fragments, or epitope-binding fragments. In particular embodiments, the anti-HLA-E antibodies are purified monospecific monoclonal antibodies. In particular embodiments, the anti-HLA-E antibodies are a mixture of two or more types of purified monospecific antibodies. In other embodiments, the anti-HLA class-E antibodies are Fab fragments.

In some embodiments, the anti-HLA-E monospecific monoclonal antibodies are IgG antibodies. In particular embodiments, the anti-HLA-E antibodies are IgG1 antibodies. In particular embodiments, the anti-HLA-E antibodies are IgG2a antibodies. In particular embodiments, the anti-HLA-E antibodies are IgG3 antibodies.

In some embodiments, the anti-HLA-E monospecific monoclonal antibodies, that are IgG antibodies may conjugated to small molecules, either synthetic or biologic or pharmaceutical grade drugs, with anti-tumor cytotoxic capabilities, for in vivo localization of tumor tissues via HLA-E expression on tumor cells to target and kill tumor cells.

In one aspect, the monospecific HLA-E antibodies can be used to localize or identify the presence of HLA-E in a cell, a tissue, an organ or a patient. Any suitably produced mammalian antibodies can be used for localization or diagnostic purposes, including but not limited to those from a mouse, a rabbit, or a human.

While not intending to be bound by any particular theory of operation, certain aspects provided herein are based, at least in part, on the identification of a potent usefulness for specific localization of HLA-E at cellular, sub-cellular and at molecular level on malignant tumor cells and non-malignant inflammatory tissues without any ambiguity or cross reactivity with other similar HLA class I alleles. The unique monospecificity of the monoclonal IgG antibodies increase the immunodiagnostic potential of the mAb for immunohistopathological demonstration of overexpression of HLA-E on tumor cells, which is critical since its expression affects survival of the patients and since it interacts with cytotoxic T cells to suppress their potential antitumor activity.

Further, while not intending to be bound by any particular theory of operation, certain aspects provided herein are based, at least in part, on the specific identification of immunoreactivity of different HLA-E monospecific mouse monoclonal antibodies to free and β2-microglobulin-associated heavy chains of HLA-E on Tumor tissue biopsies (e.g., FIG. 5). Peptide inhibition experiments indicate that these monoclonal antibodies recognize HLA-E specific epitopes (not found on HLA-A/-B/-C/-F & -G) located on α1 and α2 helices of both free and β2-microglobulin-associated heavy chains of HLA-E (e.g., Table 2).

Further, while not intending to be bound by any particular theory of operation, certain aspects provided herein are based, at least in part, on the identification of CD8+ cytotoxic T-cell proliferative immunomodulatory activity of HLA-E monospecific monoclonal antibodies (e.g., FIGS. 6-11 and Table 4).

Provided herein, in certain aspects, are mouse, chimeric, humanized or human monospecific anti-HLA-E antibody with CD8+ cytotoxic T-cell proliferative immunomodulatory activity.

In one aspect, the monospecific HLA-E antibodies can be used to block binding to HLA-E expressed on a tumor cell surface and thereby restoring the cytotoxic capabilities of CD8+ T-lymphocytes and Natural Killer T-cells ("NKT") targeting the tumor cells.

In one aspect, the monospecific HLA-E antibodies can be used to clear and eliminate soluble HLA-Es that are capable of arresting the cytotoxic capabilities of CD8+ T-lymphocytes and NKT cells targeting cancer cells.

In some embodiments, pharmaceutical compositions provided herein are used to block binding to free and (β2m-associated HLA-E on tumor cell surfaces. In some embodiment, the pharmaceutical compositions block anti-tumor efficacious HLA-E ligand binding to CD94 and NKG2a cytotoxic inhibitory receptors located on tumor infiltrating and circulatory cytotoxic CD8+ T lymphocytes and NKG2a cells (e.g., FIGS. 1A and 1B).

In some embodiments, the monospecific anti-HLA-E antibodies comprise IgG antibodies that can be administered to boost production of CD8+ Cytotoxic T cells so that producing large number cytotoxic T-cells may facilitate killing tumor cells and increase disease-free and overall survival of patients, as has been clinically documented in ovarian/cervical cancers.

In one aspect, the monospecific HLA-E antibodies provided herein can be used to augment the production of antibody against tumor-associated antigens. In some embodiments, the anti-tumor antibody production by memory B cells is augmented.

In one aspect, the monospecific HLA-E antibodies provided herein can be used to augment the production of CD8+ cytotoxic T-lymphocytes and Natural Killer T cells.

In one aspect, provided herein are methods for treating patients with early and late stages of human cancer by facilitating CD8+ T-lymphocytes (cytotoxic T-lymphocytes or CTL) and NKT cell mediated killing.

In some embodiments, the anti-HLA-E monospecific IgG1 antibodies can administered to boost production of CD8+ Cytotoxic T cells so that producing large number cytotoxic T-cells may facilitate killing tumor cells and increase disease-free and overall survival of patients and anti-HLA-E monospecific IgG3 antibodies to target and kill the tumor cells to invite complement molecules to mediate complement mediated cytotoxicity (CDC). Even if such CDC is prevented by the overexpression of complement restriction factors (CRFs: CD46 CD55, CD59) present on tumor cells the antibody binding would block the HLA-E binding to CD94/NKG2a inhibitory receptors present on CD8+ T cells and NKT cells.

In some embodiments of the pharmaceutical compositions provided herein, the composition is suitable for intramuscular administration, intradermal administration, intraperitoneal administration, intravenous administration, subcutaneous administration, or any combination thereof. In some embodiments, the pharmaceutical composition is suitable for subcutaneous administration. In some embodiments, the composition is suitable for intravenous administration. In some embodiments, the composition is suitable for intramuscular administration.

In one aspect, provided herein are methods for treating patients with early and late stages of human cancer by augmenting the production of antibody against tumor-associated antigens. In some embodiments, the anti-tumor antibody production by memory B cells is augmented.

In certain embodiments, the monospecific anti-HLA-E IgG antibodies that specifically capable of inducing antibody production by interacting with human memory B cells (e.g., FIG. 12) will be administered to boost production of antibodies that can bind to tumor cell surface antigens to target and kill the tumor cells by antibody dependent cytotoxicity (ADCC) or complement dependent cytotoxicity (CDC).

4. BRIEF DESCRIPTION OF THE FIGURES AND TABLES

FIGS. 1A and 1B illustrate exemplary HLA-E epitopes of cell surface or soluble or heavy chains of HLA-E that bind to inhibitory receptors CD94/NKG2a expressed on CD8+ Cytotoxic Lymphocytes (CTL) and the Natural Killer T cells (NKT). Note that amino acid residues in HLA-E α1 helix (SEQ ID NO:15) bind to CD94, while amino acid residues in α2 helix (SEQ ID NO:21) bind to NKG2a. Most importantly, these amino acid residues in HLA-E α1 and α2 helices are recognized by the exemplary monospecific HLA-E antibodies disclosed herein. The figure illustrates the epitopes recognized by monospecific HLA-E antibodies and CD94/NKG2a receptors. Exemplary residues that are involved in interactions between HLA-E α1 and α2 helices and CD94/NKG2a receptors are marked by grey shade. HLA-E monoclonal antibodies that do not bind to these epitopes may not block the cell surface HLA-E ligands that bind to inhibitory receptor CD94/NKG2a of CD8+ Cytotoxic Lymphocytes (CTL) and the Natural Killer T cells (NKT). Also depicted are residues in the HLA-G α1 helix (SEQ ID NO:17), the HLA-G α2 helix (SEQ ID NO:23), the HLA-F α1 helix (SEQ ID NO:16), and the HLA-F α2 helix (SEQ ID NO:22), and further sequences from CD94 (SEQ ID NO: 26), HLA-E (SEQ ID NO:27), and NKG2a (SEQ ID NO:28).

FIG. 2 depicts the variations in HLA-E reactivity (expressed as Trimmed Mean Florescent Intensity) of exemplary monospecific HLA-E antibodies (PTER-033, PTER-034, PTER-073, PTER-074 & PTER-145) during different steps of preparation. Profiles of culture supernatant, eluates obtained after Protein-G purification and the same eluates after concentration, selective centrifugation.

FIG. 3 documents the profiles emerging from the titration of HLA-E reactivity (expressed as Trimmed Mean Florescent Intensity) of concentrated Protein-G purified eluates of exemplary monospecific HLA-E antibodies (PTER-033, PTER-034, PTER-073, PTER-074 & PTER0145). MFI 1000 is used to determine the titer (which reflects the potency) of different monoclonal antibodies. Based on the estimates the titers of different antibodies can be ranked as follows: PTER-034 [200], PTER-074 [300], PTER-073 [500], PTER-033 [1000] & PTER-145 [>5000]. These titer values are valuable for developing potential HLA-E monospecific immunodiagnostic reagents. After Protein-G elution, the protein concentration of the monoclonal antibodies used are indicated at 1/10 dilution in ng. The titer values can be used to grade the exemplary monoclonal antibodies for immunodiagnosis. However, the immunomodulatory functions may differ with different antibodies, possibly depending on the specific and length of the epitope they recognize on cell surface HLA-E.

FIG. 4 illustrates dosimetric inhibition of exemplary monospecific HLA-E monoclonal antibody (PTER-033) with HLA-E peptide epitope sequences $^{65}$RSARDTA$^{71}$ (SEQ ID NO:3) and $^{143}$SEQKSNDASE$^{152}$ (SEQ ID NO:11) at varying concentrations. The linear dosimetric inhibition confirms that the epitope located in α2 helix may be specific domain recognized by PTER-033 than that located in α1 helix.

FIG. 5 documents specific immunostaining of HLA-E expressed on tumor cells with anti-HLA-E mAb. Culture supernatants of exemplary monospecific HLA-E antibodies (PTER-033, PTER-034, PTER-073, PTER-074, PTER-145) were used at V2 dilution. MEM-E/02, a HLA-E non-specific commercially concentrated mAb (reacts with several HLA-Ia alleles). Note the non-specific and background staining by MEM-E/02 and clear specific staining with the exemplary monospecific HLA-E monoclonal antibodies. Staining with the exemplary mAbs are reliable because of monospecificity of the monoclonal antibodies for HLA-E only. Serial paraffin sections of tumor biopsies of Melanoma-(AJCC Stage II; T2N0M0) surgically resected from left arm of 75 yr female was used for immunodiagnosis.

FIG. 6 shows the number of activated CD8+ T-lymphoblasts after exposure to exemplary monospecific HLA-E monoclonal antibody PTER-033 at two different concentrations or dilutions (1/30 & 1/150) in the presence or absence of Phytohemagglutin, conventionally added to stimulate T cells. Note that stimulation or activation of CD8+ T lymphocytes occur even without PHA suggesting the immunomodulatory potential of the exemplary HLA-E monospecific monoclonal antibody.

FIG. 7 shows the number of activated CD8+ T-lymphoblasts after exposure to exemplary monospecific HLA-E monoclonal antibody PTER-034 at two different concentrations or dilutions (1/10 & 1/50) in the presence or absence of Phytohemagglutin, conventionally added to stimulate T cells. Note that stimulation or activation of CD8+ T lymphocytes occur even without PHA suggesting the immunomodulatory potential of the exemplary monospecific HLA-E monoclonal antibody.

FIG. 8 shows the number of activated CD8+ T-lymphoblasts after exposure to exemplary monospecific HLA-E monoclonal antibody PTER-073 at two different concentrations or dilutions (1/10 & 1/50) in the presence or absence of Phytohemagglutin, conventionally added to stimulate T cells. Note that stimulation or activation of CD8+ T lymphocytes occur even without PHA suggesting the immunomodulatory potential of the exemplary monospecific HLA-E monoclonal antibody.

FIG. 9 shows the number of activated CD8+ T-lymphoblasts after exposure to exemplary monospecific HLA-E monoclonal antibody PTER-074 at two different concentrations or dilutions (1/10 & 1/50) in the presence or absence of Phytohemagglutin, conventionally added to stimulate T cells. Note that stimulation or activation of CD8+ T lymphocytes occur even without PHA suggesting the immunomodulatory potential of the exemplary monospecific HLA-E monoclonal antibody.

FIG. 10 shows the number of activated CD8+ T-lymphoblasts after exposure to exemplary monospecific HLA-E monoclonal antibody PTER-145 at two different concentrations or dilutions (1/10 & 1/50) in the presence or absence of Phytohemagglutin, conventionally added to stimulate T cells. Note that stimulation or activation of CD8+ T lymphocytes occur even without PHA suggesting the immunomodulatory potential of the exemplary monospecific HLA-E monoclonal antibody.

FIG. 11 shows comparison of CD8+ T-cell proliferative potential of different exemplary monospecific HLA-E monoclonal antibodies, PTER0033 (Rank #1), PTER0034 (Rank #2), PTER0073 (Rank #3, PTER0074 (Rank #4) & PTER0145 (Rank #5) at two different concentrations or dilutions (without PHA). Ranking is based on the statistical difference between mAb exposed and unexposed CD8+ T cells. Note that stimulation or activation of CD8+ T lymphocytes occur even without PHA suggesting the immunomodulatory potential of the exemplary monospecific HLA-E monoclonal antibody. Also note that mAb potentially useful for immunodiagnosis (PTER-0145) is not potential immunomodulator, whereas PTER-0033 is a potential generator of CD8+ T-lymphoblasts.

FIG. 12 proof of principle illustration on the induction of IgG antibody production by memory B cells isolated from normal healthy individuals expressing antibodies to HLA class II antigens, DR2 and DR4. Upon isolation the B cells were cultured in the presence of cytokines (IL-2, IL-4 and anti-CD40 ligand). No HLA-E specific mAbs were added in control wells, whereas in the experimental well PTEG-0019 mAb was added after Protein G elution and concentration of the hybridoma culture supernatants. The antibody secreted by the memory B cells were recovered from culture chambers recovered at 0 hr, 12 hr, 24 hr, 48 hr and 72 hr and tested against microbeads coated with DR2 or DR4 using Luminex Flow cytometry. The values show that the anti-HLA-E monospecific mAb augmented the production of IgG antibodies against DR2 and DR4.

Table 1 illustrates exemplary peptide sequences or epitopes that are shared between HLA-E and HLA class Ia epitopes.

Table 2 shows the peptide sequences or epitopes specific only for HLA-E, a critical determinant that encouraged the search for monospecific HLA-E antibodies for diagnostic purposes, since the currently available commercial ant-HLA-E mAbs show tremendous HLA-Ia reactivity (e.g., Ravindranath et al., 2010, Mol. Immunol. 47: 1121-1131 and Ravindranath et al., 2011, Mol. Immunol. 48:423-428) HLA-E specific epitopes shed light on the unique functional capabilities of HLA-E and the nature of antibodies that may bind to these epitopes, which are not only important for specific immunodiagnosis of the HLA-E in malignant and inflamed tissues but also to unravel their specific immunomodulatory efficacy. Amino acids in the α1 and α2 helices are important since they are involved in functions related to antigen presentation and binding to inhibitory or activating ligands on other immune cells including CD8+ T cells and NKT cells.

Table 3 provides the list of exemplary monospecific HLA-E monoclonal antibodies and their isotypes. Of the 258 clones developed, only 24 of them produced antibodies monospecific of HLA-E as indicated by the mean fluorescent intensities for HLA-E, HLA-F, HLA-G, HLA-A, HLA-B and HLA-Cw. The MFI of the culture supernatants of different mAbs varied very much and they are listed in the table. Exemplary monospecific HLA-E antibodies PTER-033, PTER-034, PTER-073, PTER-074 & PTER-145 were selected to study their potential for immunodiagnosis and for immunomodulation studies reported herein.

Table 4 compares the effects of different exemplary HLA-E monospecific monoclonal antibodies (PTER-033, PTER-034, PTER-073, PTER-074 & PTER-145) at two different concentrations or dilutions in the presence or absence of PHA) on CD3+ T-lymphoblasts and naïve T cells. The effects of the exemplary HLA-E monospecific monoclonal antibodies are also compared with an exemplary HLA-E nonspecific monoclonal antibody (PTER-007). Note that stimulation or activation of CD8+ T lymphoblasts occur even without PHA suggesting the proliferative potential of the exemplary HLA-E monospecific monoclonal antibody. Also note that mAb potentially useful for immunodiagnosis (PTER-145) is not potential immunomodulator, whereas PTER-033 and PTER-034 are potential generators of CD8+ T-lymphoblasts. In the absence of PHA, these mAbs do not influence CD4+/CD8− or CD4+/CD8+ T cells. However, total number of lymphocytes is invariably augmented by mAbs PTER-033 and PTER-034 both in the presence and in the absence of PHA. Stimulation of CD8+ naïve T cells are also observed with HLA-E specific mAb, however it was significant only for PTER-034 and PTER-145 at specific dilutions. The nonspecific HLA-E mAb PTER-007 suppresses CD4+ T lymphocytes at higher concentration (1/10).

5. DETAILED DESCRIPTION OF THE EMBODIMENTS

5.1. Definitions

As used herein, "administer" or "administration" refers to the act of injecting or otherwise physically delivering a substance as it exists outside the body (e.g., a pharmaceutical composition described herein) into a patient, such as by, but not limited to, pulmonary (e.g., inhalation), mucosal (e.g., intranasal), intradermal, intravenous, intramuscular delivery and/or any other method of physical delivery described herein or known in the art. When a disease, or symptoms thereof, is being treated, administration of the substance typically occurs after the onset of the disease or symptoms thereof. When a disease, or symptoms thereof, is being prevented, administration of the substance typically occurs before the onset of the disease or symptoms thereof.

The term "monospecific HLA-E antibodies," "monospecific anti-HLA-E" or "monospecific anti-HLA-E antibodies") refers to antibodies, including both modified antibodies and unmodified antibodies that bind to a monospecific epitope or amino acid sequence (either continuous or discontinuous) found only on HLA-E heavy chain (HC) polypeptide. The "monospecific HLA-E antibodies" or "monospecific anti-HLA-E" do not bind to any other HLA-Ia or HLA-Ib alleles. In some embodiments, the term "monospecific HLA-E antibodies," "monospecific anti-HLA-E" or "monospecific anti-HLA-E antibodies") also refers to antibody fragments that are immunoreactive to HLA-E and bind monospecifically to HLA-E. Ther terms antibodies is used interchangeably with "Abs." When the antibodies are monoclonal, the terms "mAb" and "mAbs" are also used. Binding between HLA-E and "monospecific HLA-E antibodies" or "monospecific anti-HLA-E" can be determined using experimental immunoassays known to those skilled in the art. Immunoassays combine the principles of immunology and biochemistry enabling tests, which include but are not limited to RIAs (radioimmunoassays), enzyme immunoassays like ELISAs (enzyme-linked immunosorbent assays), LIAs (Luminescent immunoassays) and FIAs (fluorescent immunoassays). Antibodies used in the aforementioned assays, for instance primary or secondary antibodies, can be labeled with radioisotopes (e.g., 125I), fluorescent dyes (e.g., PC or FITC) or enzymes (e.g., peroxidase or alkaline phosphatase), which catalyze fluorogenic or luminogenic reactions. See e.g., Eleftherios et al., 1996, Immunoassay, Academic Press; Law et al., 2005, Immunoassay: A Practical Guide, Taylor & Francis; Wild et al., 2005, The Immunoassay Handbook, Third Edition, Elsevier; Paul et al., 1989, Fundamental Immunology, Second Edition, Raven Press, for a discussion regarding antibody specificity.

Antibodies provided herein include any form of antibody known to those skilled in the art. In some embodiments, the monospecific HLA-E antibodies provided herein include, but are not limited to, mammalian antibodies (e.g., mouse or rabbit antibodies), human antibodies, humanized antibodies, chimeric antibodies, intrabodies, synthetic antibodies, monoclonal antibodies, a mixture of multiple monoclonal antibodies targeting the same or different epitopes, recombinantly produced antibodies, multispecific antibodies, single-chain Fvs (scFvs; e.g., including monospecific, bispecific, etc.), Fab fragments, F(ab') fragments, disulfide-linked Fvs (sdFv), anti-idiotypic (anti-Id) antibodies, and epitope-binding fragments of any of the above. Antibodies provided herein include both modified antibodies (i.e., antibodies that comprise a modified IgG (e.g., IgG1) constant domain, or FcRn-binding fragment thereof, (e.g., the Fc-domain or hinge-Fc domain) and unmodified antibodies (i.e., antibodies that do not comprise a modified IgG (e.g., IgG1 constant domain). In particular, antibodies include immunoglobulin molecules and immunologically active portions of immunoglobulin molecules.

In some embodiments, monospecific HLA-E antibodies provided herein can be of any subclass of IgG (e.g., IgG1, IgG2: IgG2a and IgG2b, IgG3, IgG4).

The term "HLA-E antigen," with respect to the monospecific HLA-E antibodies or monospecific anti-HLA-E, refers to the HLA heavy chain or portion of the HLA heavy chain that is bound to another HLA-E heavy chain to form a homodimer, or an HLA-E heavy chain associated with a β2-microglobulin to form a heterodimer or an HLA-E heavy chain or portion of an HLA-E heavy chain that is free (i.e., not bound to another HLA or β2-microglobulin). HLA-E antigens can be found on an HLA heavy chain when it is expressed or located on a cell surface or when it exists in soluble form in circulation or body fluids.

The term "constant domain" refers to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

The term "effective amount" as used herein refers to the dose or amount required for treatment (e.g., an antibody provided herein) which is sufficient to reduce and/or ameliorate the severity and/or duration of any one of the disease or conditions described herein. In some embodiments, the effective amount of an antibody of the pharmaceutical composition provided herein is between about 0.025 mg/kg and about 60 mg/kg body weight of a human subject. In some embodiments, the effective amount of an antibody of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

The term "epitopes" as used herein refers to continuous or discontinuous peptide sequence or sequences or fragments of an HLA-E allele polypeptide recognized by the Fab portion of the antibody, and having immunogenic activity in an animal, preferably a mammal, and most preferably in a human. An epitope having immunogenic activity is a fragment of a polypeptide that elicits an antibody response in an animal or in a human. See Table 2 for specific epitope sequences of HLA-E.

The term "excipients" as used herein refers to inert substances which are commonly used as a diluent, vehicle, preservatives, binders, or stabilizing agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). Also see Remington et al., 1990, Remington's Pharmaceutical Sciences, Mack Publishing Co, which is hereby incorporated in its entirety.

In the context of a peptide or polypeptide, the term "fragment" as used herein refers to a peptide or polypeptide comprising an amino acid sequence of at least 5 contiguous amino acid residues, at least 10 contiguous amino acid residues, at least 15 contiguous amino acid residues of the amino acid sequence of a particular polypeptide to which an antibody immunospecifically binds.

The terms "IgG Fc region," "Fc region," "Fc domain," "Fc fragment" and other analogous terms as used herein refer the portion of an IgG molecule that correlates to a crystallizable fragment obtained by papain digestion of an IgG molecule. The Fc region consists of the C-terminal half of the two heavy chains of an IgG molecule that are linked by disulfide bonds. It has no antigen binding activity but may or may not contain carbohydrate moiety and the binding sites for complement and Fc receptors, including the FcRn receptor (see below).

The term "immunomodulatory agent" and variations thereof including, but not limited to, immunomodulatory agents, as used herein refer to an agent that modulates one or more of the components (e.g., immune cells, or subcellular factors, genes regulating immune components, cytokines, chemokines or such molecules) of a host's immune system. In certain embodiments, an immunomodulatory agent is an immunosuppressive agent. In certain other embodiments, an immunomodulatory agent is an immunostimulatory agent. HLA-e monospecific monoclonal antibodies are considered as Immunomodulatory agents.

An "isolated" or "purified" antibody is substantially free of cellular material or other contaminating proteins or other antibodies. The language "substantially free of cellular material" includes preparations of an antibody in which the antibody is separated from cellular components of the cells from which it is isolated or recombinantly produced. When the antibody is recombinantly produced, it can also be substantially free of culture medium. When the antibody is produced by chemical synthesis, it can also be substantially free of chemical precursors or other chemicals, i.e., it is separated from chemical precursors or other chemicals which are involved in the synthesis of the protein. In a specific embodiment, antibodies provided herein are isolated or purified.

As used herein, the terms "manage," "managing," and "management" refer to the beneficial effects that a subject derives from a therapy (e.g., a prophylactic or therapeutic agent), which does not result in a cure of the disease or condition described herein.

As used herein, the term "modified antibody" encompasses any antibody described herein that comprises one or more "modifications" to the amino acid residues at given positions of the antibody constant domain (e.g., an IgG or an IgG1 constant domain), or FcRn-binding fragment thereof wherein the antibody has an increased in vivo half-life as compared to known antibodies and/or as compared to the same antibody that does not comprise one or more modifications in the IgG constant domain, or FcRn-binding fragment thereof. As used herein, a "modified antibody" may or may not be a high potency, high affinity and/or high avidity modified antibody. In certain embodiments, the modified antibody is a high potency antibody. In certain embodiments, the modified antibody is a high potency, high affinity modified antibody. In certain embodiments, the modified antibody may imply monoclonal antibodies conjugated with toxins, drugs and small molecules.

The term "pharmaceutically acceptable" as used herein means being approved by a regulatory agency of the Federal or a state government, or listed in the U.S. Pharmacopia, European Pharmacopia or other generally recognized pharmacopia for use in animals, and more particularly in humans.

As used herein, the terms "prevent," "preventing," and "prevention" refer to the total or partial inhibition of any of the diseases or conditions described herein.

The terms "stability" and "stable" as used herein in the context of a liquid formulation comprising an antibody provided herein refer to the resistance of the antibody in the formulation to thermal and chemical unfolding, aggregation, degradation or fragmentation under given manufacture, preparation, transportation and storage conditions. The "stable" formulations of the antibodies and pharmaceutical compositions provided herein retain biological activity equal to or more than 80%, 85%, 90%, 95%, 98%, 99%, or 99.5% under given manufacture, preparation, transportation and storage conditions. The stability of the antibody can be assessed by degrees of aggregation, degradation or fragmentation by techniques known to those skilled in the art, including but not limited to reduced Capillary Gel Electrophoresis (rCGE), Sodium Dodecyl Sulfate Polyacrylamide Gel Electrophoresis (SDS-PAGE) and HPSEC. The overall stability of a formulation comprising an antibody that immunospecifically binds to an HLA-E antigen can be assessed by various immunological assays including, for example, ELISA and radioimmunoassay using the entire or part of the polypeptide of HLA-E.

As used herein, the terms "subject" and "patient" are used interchangeably. In some embodiments, the subject is a human and in others it is an animal.

The term "substantially free of surfactant" as used herein refers to a formulation of a pharmaceutical composition, said formulation containing less than 0.0005%, less than 0.0003%, or less than 0.0001% of surfactants and/or less than 0.0005%, less than 0.0003%, or less than 0.0001% of surfactants.

The term "substantially free of salt" as used herein refers to a formulation of a pharmaceutical composition, said formulation containing less than 0.0005%, less than 0.0003%, or less than 0.0001% of inorganic salts.

The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials.

As used herein, the term "therapeutic agent" refers to any agent that can be used in the treatment, management or amelioration of one of the diseases or conditions described herein.

As used herein, the term "therapy" refers to any protocol, method and/or agent that can be used in the prevention, management, treatment and/or amelioration of one of the diseases or conditions described herein.

In certain embodiments provided herein, the term "therapeutically effective" with respect to the pharmaceutical composition, refers to the ability of the composition to reduce the severity, the duration and/or the symptoms of a particular disease or condition.

As used herein, the terms "treat," "treatment" and "treating" refer to the reduction or amelioration of the progression, severity, and/or duration of one of the conditions described herein.

5.2. HLA-E Monospecific Antibodies: Characteristics

The cross reactivity of anti-HLA-E mAbs to HLA-A, -B or -Cw is likely due to recognition of shared epitopes found between HLA-E and HLA-Ia alleles. Thus, it was proposed that a monoclonal antibody binding to epitopes unique to HLA-E can be designated as truly monospecific HLA-E antibodies. Such antibodies, being only monospecific for HLA-E, are likely to be more reliable and invaluable for immunodiagnosis of HLA-E in normal and pathological tissue samples overexpressing HLA-E such as the human cancer cells described.

Table 2 shows 4 peptide sequences that can be recognized by HLA-E-specific monoclonal antibodies. The 4 peptide sequences include both helical and non-helical amino acid sequences. They are presented in Table 2 in comparison with the amino acid sequences from corresponding positions in HLA-F and HLA-G. Amino acid sequences from corresponding positions in HLA-A, HLA-B and HLA-Cw are too varied and show little or no consensus. Among these 4 sequences, two peptides in the α-helical regions were found to be very specific for HLA-E and not found in other non-classical HLA-Ib alleles, namely HLA-F and HLA-G. The peptides are: $^{65}$RSARDTA$^{71}$ (SEQ ID NO:3) and $^{143}$SEQKSNDASE$^{152}$ (SEQ ID NO:11) (Ravindranath et al., 2010, Mol. Immunol. 47. 1663-1664).

Peptides monospecific for HLA-E are recognized by monoclonal antibodies which bind only with HLA-E but not to HLA-A/-B/-C/-F or -G (Table 2). Most interestingly, the amino acids in the α1 helix of HLA-E that bind to CD94 receptor and those in the α2 helix in HLA-E that bind to NKG2a receptor are found in the amino acid sequences of HLA-E specific or restricted epitopes.

In one aspect, provided herein are chimeric, humanized or human anti-HLA-E IgG antibodies that are specifically immunoreactive to the heavy chain polypeptide of HLA-E but not immunoreactive to the heavy chain polypeptide of HLA-A, HLA-B, HLA-Cw, HLA-F, HLA-G or β2-microglobulin or any HLA class II alleles. Also provided herein are pharmaceutical compositions comprising such antibodies in a pharmaceutically acceptable carrier.

HLA-E has two major alleles: HLA-E$^{R107}$ and HLA-E$^{G107}$. Both are found in every human being. They are co-dominantly expressed on the cell membrane as a pair of alleles. HLA-E molecules can bind and present peptide antigens produced intracellularly, including those from viral and tumor specific proteins, to CD8+ effector T-cells (e.g., cytotoxic T-cells (CTLs)). In response to foreign antigens presented by HLA-E, CD8+ effector T-cells can destroy the cells presenting the foreign antigen.

An HLA-E molecule can be expressed on a cell surface as a heavy chain (HC) by itself or as an HC non-covalently linked to β2-microglobulin ("β2 m"). HC consists of three extracellular domains (α1, α2 and α3), a transmembrane domain and a C-terminal cytoplasmic domain. Such HLA molecules can be expressed without β2m on the cell surface on activated T-lymphocytes, CD 14+ blood monocytes, activated dendritic cells of healthy individuals and in cells and tissues of patients with inflammatory diseases (see, for example, Schnabel et al., 1990, J. Exp. Med. 171: 1431-1432; Raine et al., 2006, Rheumatology 45: 1338-1344; Raine et al., 2006, Rheumatology 45: 1338-1344; and Tsai et al., 2002, Rheumatology 29: 966-972). On the cell surface, HC and β2m can dissociate, leaving membrane bound HC only (Machold, et al., 1996, J. Exp. Med. 184: 2251-2259; Carreno et al., 1994, Eur. J. Immunol. 24: 1285-1292; Parker et al., 1992, J. Immunol. 149: 1896-1904). On the cell surface, the HC of an HLA can occur in different conformations (Marozzi et al. 1996, Immunogenetics, 43: 289-295). The HC of HLA molecules can be released by metalloproteases from the cell surface into surrounding media and circulation (Demaria et al., 1994, J. Biol. Chem. 269: 6689-6694). In circulation, in blood and in other body fluids, HLA molecules can occur as soluble fraction (heavy chains free or associated with β2-microglobulin) of different molecular weights (47, 42, 35 kDa). Soluble HLA (e.g., sHLA-E) can trigger cell death of CD8+ Cytotoxic T-lymphocytes and NK cells impair NK cell functions. See Demaria et al., 1993, Int J Clin Lab Res. 23:61-9; Puppo et al., 2000, Int Immunol. 12:195-203; Puppo et al., 2002, ScientificWorldJournal. 2:421-3; Contini et al., 2000, Hum Immunol. 61:1347-51; Contini et al., 2003, Eur J. Immunol. 33:125-34; Spaggiari et al., 2002, Blood 99:1706-14; Spaggiari et al., 2002, Blood 100:4098-107.

Anti-HLA-E antibodies described herein are specifically immunoreactive only to HLA-E and not immunoreactive to the heavy chain polypeptide of HLA-A, HLA-B, HLA-Cw, HLA-F, HLA-G or β2-microglobulin or any HLA class II alleles (see, Table 3). In addition, the peptide epitope through which an antibody binds to an HLA can be assessed by inhibiting the antibody binding to the HLA using the same peptide sequence or epitope (see FIG. 4)

Monospecific HLA-E IgG antibodies can be produced by murine hybridoma technology and several clones that secrete antibodies with diversified specificity can be generated. For example, 258 hybridoma clones have been generated by immunizing Balb/c mice with two different alleles of HLA-E: HLA-E$^{R107}$ and HLA-E$^{G107}$ (clones with specific activities against HLA-E are listed in Table 3). The hybridoma produced from these two different alleles may react to heavy chain (HC) polypeptides of HLA-E only or to HC polypeptides of HLA-F and/or HLA-G and/or HLA-A and/or HLA-B and/or HLA-Cw. By clonal selection, clones secreting IgG antibodies can be generated (of different subclasses) reacting only to HLA-E but not to any other HLA.

Using genome of the clones, chimeric or humanized antibodies can be generated by different methods known in the art for the synthesis of antibodies, in particular, by chemical synthesis or by recombinant expression techniques. These methods employ, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al., 1982, Molecular Cloning: A Laboratory Manual, Cold Spring Harbor Laboratory Press; Sambrook et al., 1989, Molecular Cloning: A Laboratory Manual, Second Edition, Cold Spring Harbor Laboratory Press; Ausubel et al., 1987 and annual updates, Current Protocols in Molecular Biology, John Wiley & Sons; Gait ed., 1984, Oligonucleotide Synthesis: A Practical Approach, IRL Press; Eckstein ed., 1991, Oligonucleotides and Analogues: A Practical Approach, IRL Press; Birren et al., 1999, Genome Analysis: A Laboratory Manual, Cold Spring Harbor Laboratory Press.

Chimeric antibodies described herein can be produced by any technique known to those of skill in the art. See, e.g., Morrison, 1985, Science 229: 1202; Oi et al., 1986, BioTechniques 4: 214; Gillies et al., 1989, J. Immunol. Methods 125: 191-202; and U.S. Pat. Nos. 5,807,715; 4,816,567; 4,816,397; and 6,331,415, each of which is incorporated herein by reference in its entirety.

Human antibodies described herein can be produced by any method known in the art, including but not limited to methods described in International Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in its entirety.

Humanized antibodies described herein can be produced using any technique known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5): 489-498; Studnicka et al., 1994, Protein Engineering 7(6): 805-814; and Roguska et al., 1994, PNAS 91: 969-973), chain shuffling (U.S. Pat. No. 5,565,332), and techniques disclosed in, e.g., U.S. Pat. No. 6,407,213; U.S. Pat. No. 5,766,886; WO 9317105; Tan et al., 2002, J. Immunol. 169: 1119 25; Caldas et al., 2000, Protein Eng. 13(5): 353-60; Morea et al., 2000, Methods 20(3): 267 79; Baca et al., 1997, J. Biol. Chem. 272(16): 10678-84; Roguska et al., 1996, Protein Eng. 9(10): 895 904; Couto et al., 1995, Cancer Res. 55 (23 Supp): 5973s-5977s; Couto et al., 1995, Cancer Res. 55(8): 1717-22; Sandhu, 1994, Gene 150(2): 409-10; and Pedersen et al., 1994, J. Mol. Biol. 235(3): 959-73. See also U.S. Patent Pub. No. US 2005/0042664 A1 (Feb. 24, 2005), each of which are incorporated by reference herein in its entirety.

In some embodiments, the monospecific HLA-E antibodies are purified antibodies. Purified antibodies are substantially free of cellular material or other contaminating proteins from the cell or tissue source from which the protein is derived, or substantially free of chemical precursors or other chemicals when chemically synthesized. Methods of purifying antibodies are well known to those skilled in the art. The culture supernatant containing the anti-HLA-E IgG can be purified using Protein G column and the purified anti-HLA-E monospecific IgG can be concentrated to obtain high potency monoclonal antibodies (see example FIG. 2)

The monospecific HLA-E antibodies provided herein include, but are not limited to, synthetic antibodies, monoclonal antibodies, a mixture of multiple monospecific monoclonal antibodies, recombinantly produced antibodies, multispecific antibodies, single-chain Fvs (scFvs), Fab fragments, F(ab') fragments, disulfide-linked Fvs (sdFv), anti-idiotypic (anti-Id) antibodies, and epitope-binding fragments of any of the above. In particular embodiments, the anti-HLA-E antibodies comprise immunoglobulin molecules and immunologically active portions of immunoglobulin molecules. In particular embodiments, the anti-HLA-E antibodies comprise monoclonal antibodies. In particular embodiments, the anti-HLA-E antibodies comprise purified monoclonal antibodies. In particular embodiments, the anti-HLA-E antibodies comprise a mixture of multiple purified monoclonal antibodies. In other embodiments, the anti-HLA-E antibodies comprise Fab fragments.

Anti-HLA-E monospecific antibodies described herein can be of any subclass of IgG (e.g., IgG1, IgG2 (e.g., IgG2a and IgG2b), IgG3, IgG4) of immunoglobulin molecule. In some embodiments, the anti-HLA-E antibodies are IgG1 antibodies.

Anti-HLA-E monospecific antibodies include both modified antibodies (i.e., antibodies that comprise a modified IgG (e.g., IgG1) constant domain, or FcRn-binding fragment thereof (e.g., the Fc-domain or hinge-Fc domain) and unmodified antibodies (i.e., antibodies that do not comprise a modified IgG (e.g., IgG1) constant domain, or FcRn-binding fragment thereof (e.g., the Fc-domain or hinge-Fc domain)), that bind to HLA-E and not to the heavy chain polypeptide of HLA-A, HLA-B, HLA-Cw, HLA-F and HLA-G. Techniques of making modified antibodies are well known to those skilled in the art.

In some embodiments of the pharmaceutical compositions provided herein, the anti-HLA-E antibodies are modified antibodies. In some embodiments, the anti-HLA-E antibodies comprise modified IgG constant domain or FcRn-binding fragments.

In some embodiments, the anti-HLA-E monospecific antibodies are modified to increase in vivo serum half-life. In some embodiments, the anti-HLA-E monospecific antibodies comprise modified IgG constant domain or FcRn-binding fragments that increase in vivo serum half-lives of the antibodies.

In some embodiments, the anti-HLA-E antibodies are attached to inert polymer molecules to prolong in vivo serum circulation of the antibodies.

In particular embodiments, the inert polymer molecules are high molecular weight polyethyleneglycols (PEGs).

PEGs can be attached to the antibodies with or without a multifunctional linker either through site-specific conjugation of the PEG to the N- or C-terminus of the antibodies or via epsilon-amino groups present on lysine residues. In another embodiment, the anti-HLA-E antibodies are conjugated to albumin. The techniques are well-known in the art. See, e.g., International Publication Nos. WO 93/15199, WO 93/15200, and WO 01/77137; and European Patent No. EP 413,622, all of which are incorporated herein by reference.

In some embodiments, the anti-HLA-E antibodies are immunoreactive to the heavy chain polypeptide of HLA-E and are not immunoreactive to the heavy chain polypeptide of HLA-A, HLA-B, HLA-Cw, HLA-F and HLA-G, or to β2-microglobulin.

In certain embodiments, anti-HLA-E monospecific antibodies provided herein are immunoreactive to HLA-E either in native or denatured confirmation. In some embodiments, the anti-HLA-E monospecific antibodies provided herein are immunoreactive to HLA-E in native form (i.e., an HLA-E heavy chain polypeptide in native form).

In other embodiments, the anti-HLA-E monospecific antibodies provided herein are immunoreactive to HLA-E in denatured form (i.e., a denatured HLA-E heavy chain polypeptide).

5.3. HLA-E Monospecific Antibodies: Pharmaceutical Compositions

In certain embodiments, provided herein are pharmaceutical compositions comprising antibodies in a pharmaceutically acceptable carrier.

In some embodiments, the monospecific HLA-E antibodies in the pharmaceutical compositions are purified monoclonal antibodies, a mixture of multiple purified monospecific antibodies, recombinantly produced antibodies, Fab fragments, F(ab') fragments, epitope-binding fragments or a mixture thereof.

In some embodiments, the pharmaceutical composition comprises antibodies, wherein at least 30% of the antibodies are monospecific HLA-E antibodies. In some embodiments, the pharmaceutical composition comprises antibodies, wherein at least 35% of the antibodies are monospecific HLA-E antibodies.

In some embodiments, the pharmaceutical composition comprises antibodies, wherein at least 40% of the antibodies are monospecific HLA-E antibodies. In some embodiments, the pharmaceutical composition comprises antibodies, wherein at least 45% of the antibodies are monospecific HLA-E antibodies.

In some embodiments, the pharmaceutical composition comprises antibodies, wherein at least 50% of the antibodies are monospecific HLA-E antibodies. In some embodiments, the pharmaceutical composition comprises antibodies, wherein at least 55% of the antibodies are monospecific HLA-E antibodies.

In some embodiments, the pharmaceutical composition comprises antibodies, wherein at least 60% of the antibodies are monospecific HLA-E antibodies. In some embodiments, the pharmaceutical composition comprises antibodies, wherein at least 65% of the antibodies are monospecific HLA-E antibodies.

In some embodiments, the pharmaceutical composition comprises antibodies, wherein at least 70% of the antibodies are monospecific HLA-E antibodies. In some embodiments, the pharmaceutical composition comprises antibodies, wherein at least 75% of the antibodies are monospecific HLA-E antibodies.

In some embodiments, at least 80% of the antibodies are monospecific HLA-E antibodies. In certain embodiments, at least 85% of the antibodies are anti-HLA-E monospecific monoclonal antibodies.

In certain embodiments, at least 90% of the antibodies are monospecific HLA-E antibodies. In certain embodiments, at least 95% of the antibodies are monospecific HLA-E antibodies.

In certain embodiments, at least 99% of the antibodies are monospecific HLA-E antibodies. In other embodiments, at least 99.5% of the antibodies are anti-HLA-E monospecific monoclonal antibodies.

5.4. HLA-E Monospecific Antibodies: Pharmaceutically Acceptable Carriers

The pharmaceutical compositions provided herein also comprise a pharmaceutically acceptable carrier. In some embodiments, the carrier can be a diluent, excipient, or vehicle with which the pharmaceutical composition is administered.

In some embodiments, such pharmaceutical carriers can be sterile liquids, such as water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions.

In some embodiments, suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

In some embodiments, the composition, if desired, can also contain minor amounts of wetting or emulsifying agents, or pH buffering agents. These compositions can take the form of solutions, suspensions, emulsion, tablets, pills, capsules, powders, sustained-release formulations and the like.

In some embodiments, oral formulation can include standard carriers such as pharmaceutical grades of mannitol, lactose, starch, magnesium stearate, sodium saccharine, cellulose, magnesium carbonate, etc. Examples of suitable pharmaceutical carriers are described in E. W. Martin, 1990, Remington's Pharmaceutical Sciences, Mack Publishing Co.

5.5. HLA-E Monospecific Antibodies: Formulations

In some embodiments, the pharmaceutical composition is provided in a form suitable for administration to a human subject. In some embodiments, the pharmaceutical composition will contain a prophylactically or therapeutically effective amount of the anti-HLA-E monospecific monoclonal antibody together with a suitable amount of carrier so as to provide the form for proper administration to the patient. The formulation should suit the mode of administration.

In some embodiments, the pharmaceutical composition is provided in a form suitable for intravenous administration. Typically, compositions suitable for intravenous administration are solutions in sterile isotonic aqueous buffer. Where necessary, the composition may also include a solubilizing agent and a local anesthetic such as lignocamne to ease pain at the site of the injection. Such compositions, however, may be administered by a route other than intravenous administration.

In particular embodiments, the pharmaceutical composition is suitable for subcutaneous administration. In particular embodiments, the pharmaceutical composition is suitable for intramuscular administration.

Components of the pharmaceutical composition can be supplied either separately or mixed together in unit dosage form, for example, as a dry lyophilized powder or water free concentrate. Where the composition is to be administered by infusion, it can be dispensed with an infusion bottle containing sterile pharmaceutical grade water or saline. Where the composition is administered by injection, an ample of sterile water for injection or saline can be provided so that the ingredients may be mixed prior to administration.

In some embodiments, the pharmaceutical composition is supplied as a dry sterilized lyophilized powder that is capable of being reconstituted to the appropriate concentration for administration to a subject. In some embodiments, the anti-HLA-E monospecific monoclonal antibody is supplied as a water free concentrate. In some embodiments, the antibody is supplied as a dry sterile lyophilized powder at a unit dosage of at least 0.5 mg, at least 1 mg, at least 2 mg, at least 3 mg, at least 5 mg, at least 10 mg, at least 15 mg, at least 25 mg, at least 30 mg, at least 35 mg, at least 45 mg, at least 50 mg, at least 60 mg, or at least 75 mg.

In another embodiment, the pharmaceutical composition is supplied in liquid form. In some embodiments, the pharmaceutical composition is provided in liquid form and is substantially free of surfactants and/or inorganic salts. In some embodiments, the antibody is supplied as in liquid form at a unit dosage of at least 0.1 mg/ml, at least 0.5 mg/ml, at least 1 mg/ml, at least 2.5 mg/ml, at least 3 mg/ml, at least 5 mg/ml, at least 8 mg/ml, at least 10 mg/ml, at least 15 mg/ml, at least 25 mg/ml, at least 30 mg/ml, or at least 60 mg/ml.

In some embodiments, the pharmaceutical composition is formulated as a salt form. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

5.6. HLA-E Monospecific Antibodies: Diagnostic Applications

In some embodiments, HLA-E antigen is overexpressed or located on the cell surface of tumor cells or inflamed tissues. In some embodiments, HLA-E antigen either occurs as HC polypeptide or in association with β2-microglobulin in soluble form in circulation or body fluids.

Immunodiagnosis of cell surface HLA-E, for clinical or non-clinical purposes, involves intact (associated with β2-microglobulin) or heavy chain (HC) polypeptide and immunostaining of HLA-E with one of the monospecific purified and concentrated monoclonal mammalian antibodies (listed in Table 3; e.g., from a mouse, a rabbit, or a human), either conjugated to fluorescent dyes (e.g., FITC or phycoerythrin) or radiolabels (e.g., $^{125}$I) or with secondary anti-IgG antibody conjugated with fluorescent dyes (e.g., FITC or phycoerythrin) or radiolabels (e.g., $^{125}$I) with appropriate isotype controls (IgG1, IgG2a, IgG3) treated in similar manner.

Soluble HLA-E is a consequence of shedding overexpression and shedding of HLA-E heavy chains during inflammation, cancer and pregnancy. For quantitative or semi-quantitative measurements of soluble HLA-E in sera, plasma, tumor fluid, peritoneal fluids, seminal or vaginal fluids, synovial saliva, tears and such other human body fluids, animal or murine monospecific monoclonal antibodies that are capable of recognizing diverse epitopes are critically invaluable. An ELISA or microELISA system, we will use the diverse epitope specific but in general HLA-E monospecific animal or mouse monoclonal antibodies will be used as "antigen capture antibody" (to be coated on to the ELISA plates) and "detection antibody after capturing HLA-E present in the body fluids" following well known prior art of Antigen-capture indirect ELISA protocols.

Immunolocalization of soluble HLA-E, for clinical or non-clinical purposes, involves intact (associated with β2-microglobulin) or heavy chain (HC) polypeptide and immunostaining of HLA-E on Western Blots or as spot tests with one of the monospecific purified and concentrated monoclonal antibody (listed in Table 3), either conjugated to fluorescent dyes (e.g., FITC or phycoerythrin) or radiolabels (e.g., $^{125}$I) or with secondary anti-IgG antibody conjugated with fluorescent dyes (e.g., FITC or phycoerythrin) or radiolabels (e.g. $^{125}$I) with appropriate isotype controls (IgG1, IgG2a, IgG3) treated in similar manner.

The HLA-E monospecific monoclonal antibody differs from existing commercial anti-HLA-E monoclonal antibodies (e.g., MEM-series including E/02, E/06, E/07 & E/08 and 3D12) bind to several HLA-I alleles (HLA-A, HLA-B and HLA-Cw). HLA-A, HLA-B and HLA-Cw occur on normal, inflamed and malignant cell surface as pair of alleles (e.g., Pair of HLA-A, pair of HLA-B and a pair of HLA-Cw). The commercial antibodies (MEM series and 3D12) bind not only to HLA-E but also to a variety of these alleles (See, e.g., Ravindranath et al., 2010, Mol. Immunol. 47: 1121-1131 and Ravindranath et al., 2011, Mol. Immunol. 48:423-428). These known commercial antibodies were used in most of the clinical and oncological diagnosis of HLA-E. In view of their cross reactivity with other HLA-Ia alleles and lack of specificity for HLA-E, the reliability of these common commercial antibodies for diagnostic purpose of HLA-E can be limited. Moreover, in the exemplary embodiments, the tissues or cells examined by the anti-HLA-E mAbs also expressed two HLA-A alleles (homo or hetero), two HLA-B alleles (home or hetero) and two HLA-C alleles (homo or hetero). If the anti-HLA-E mAb used to diagnose of HLA-E on these tissues or cells were capable of binding to these 1 to 6 alleles, it would reveal high and diffused background after immunostaining, in contrast to the monospecific anti-HLA-E mAbs described herein. Thus, the monospecific anti-HLA-E monoclonal antibodies described herein, e.g., in Table 3, are specific and most reliable for tissue or cellular diagnosis of HLA-E, particularly when they are overexpressed on cells like tumor and inflammatory cells. FIG. 5 illustrates the proof of concept with five of such monospecific anti-HLA-E monoclonal antibodies.

In some embodiments, a diagnostic kit can be used to diagnosing or localizing HLA-E on normal or diseases cells or tissues. Such a diagnostic kit can comprise any of the monospecific HLA-E antibodies described herein. In some embodiments, such diagnosis occurs in vivo in a live patient or mammal.

In some embodiments, the diagnostic kit is used to determine the presence or stage of development of cancers, including any form of carcinoma, sarcoma, lymphoma and leukemia, germ cell tumor and blastoma.

5.7. HLA-E Monospecific Antibodies: Therapeutic Applications

As described in FIGS. 1A and 1B, HLA-E binds to both CD94 and NKG2a inhibitory receptors on CD8+ T cells and NKT cells and prevents cytotoxic capabilities of these immune cells. When an anti-HLA-E antibody binds specifically to an HLA-E expressed on the surface of a cell, it can block or prevent the activities of the cell surface HLA-E. Without being bound to any particular theory of operation, it is believed that the therapeutic efficacy of an anti-HLA-E monospecific monoclonal antibody provided herein is dependent on the unique ability of the anti-HLA-E monospecific monoclonal antibody to bind to HLA-E alleles without binding to other HLA-Ia (HLA-A, HLA-B, HLA-Cw) or HLA-Ib (HLA-F and HLA-G) alleles on the immune cells.

When an anti-HLA-E monospecific monoclonal antibody described herein binds a soluble HLA-E antigen, it can also block or prevent the activities of the soluble HLA-E from binding to an inhibitory receptors (CD94/NKG2a), on a CD8+ T-lymphocyte or Natural Killer T cells. Furthermore, an anti-HLA-E monospecific monoclonal antibody described herein that binds to a soluble HLA-E antigen in circulation or a body fluid may clear the soluble HLA-E from the circulation or body fluid before the soluble HLA-E, by its ligand-inhibitors interaction on CD8+ T-cells and Natural Killer cells, which may otherwise result in failure to induce cytotoxicity of tumor cells. Without being bound to any particular theory of operation, it is believed that the therapeutic efficacy of an anti-HLA-E monospecific monoclonal antibody provided herein is dependent on the unique ability of the anti-HLA-E monospecific monoclonal antibody to bind to HLA-E alleles without binding to other HLA-Ia (HLA-A, HLA-B, HLA-Cw) or HLA-Ib (HLA-F and HLA-G) alleles on the immune cells.

Several investigators have shown that high number of CD8+ T lymphocytes in tumor microenvironment has tremendous anti-tumor implication. For example, Gooden et al have shown in ovarian and cervical cancer, patients with high number of CD8+ T lymphocytes survive better. See Gooden M et al., 2011, Proc Natl Acad Sci USA. 108:10656-10661. The survival is much better if HLA-E is down regulated to prevent their interaction with both CD94 and NKG2a inhibitory receptors on CD8+ T cells and NKT cells that lower the cytotoxic capabilities of these immune cells.

In particular, findings of Gooden et al (2011) in patients with ovarian and cervical cancer support the relevance and pertinence of this example for therapeutic application of HLA-E-monospecific monoclonal antibodies for treatment of Cancer patients. In addition, most of the cancer types overexpress HLA-E and the overexpression paralyzes the CD8+ T cells and NKT cells in the tumor microenvironment from cytotoxic killing of tumor cells. Oncologists investigated HLA-E protein expression on tissue sections of 420 ovarian and cervical cancers and found equal or higher levels than normal counterpart epithelia in 80% of the tumors. In situ detection of HLA-E interacting receptors revealed a very low infiltrate of NK T-cells, but up to 50% of intraepithelial CD8+ Cytotoxic T cells (CTLs) expressed the inhibiting CD94/NKG2A receptor. In cervical cancer, HLA-E expression did not alter the prognostic effect of CTLs, most likely due to very high infiltrating CTL numbers in this virus-induced tumor. Overall survival of ovarian cancer patients, however, was possibly influenced by HLA-E, because the beneficial effect of high CTL infiltration was completely neutralized in the subpopulation with strong HLA-E expression. These results indicate that CTL infiltration in ovarian cancer is associated with better survival only when HLA-E expression is low and that intratumoral CTLs are inhibited by CD94/NKG2A receptors on CTLs in the tumor microenvironment.

FIGS. 6 to 11 show that different monospecific anti-HLA-E monoclonal antibodies, described herein (e.g., Table 3) can augment the number of CD8+ T lymphoblasts and some at the level of naïve CD8+ T lymphocytes both in the absence and presence of Phytohemagglutin (PHA), an activator of T cells. The monoclonal antibodies described herein are capable of induce proliferation CD8+ T lymphoblasts and some at the level of naïve CD8+ T lymphocytes in the absence of PHA, which strongly supports the unique CD8+ T cell proliferative potential of these monospecific monoclonal antibodies. Therefore it is envisaged that these monoclonal antibodies when administered as chimeric or humanized monospecific monoclonal antibodies in cancer patients may augment the production of cytotoxic CD8+ T cells.

In some embodiments, the immunoreactivity of the anti-HLA-E monospecific monoclonal antibodies can be blocked by one or more particular peptides comprising an amino acid sequence listed in Table 2 or combinations thereof.

The amino acid sequences listed in Table 2 are amino acid sequences (with the exception of two sequences: RSARDTA (SEQ ID NO: 3) and SEQKSNDASE (SEQ ID NO: 11) that were found specific for HLA-E and not shared by any of the other HLAs namely HLA-A, HLA-B, HLA-Cw, HLA-F and HLA-G (see Table 2). Thus, while not being bound to any particular theory of operation, it is believed that in some embodiments, the immunoreactivity of the anti-HLA-E monospecific monoclonal antibodies can be blocked by polypeptides having at least one of these amino acid sequences.

Without being bound to any particular theory of operation, it is believed that the pharmaceutical compositions described herein can augment or promote proliferation and/or blastogenesis of naïve and/or activated CD8+ T-cells in a recipient of the pharmaceutical composition. See, e.g., FIGS. 5 to 11.

In some embodiments provided herein, the pharmaceutical composition described herein can augment or promote proliferation and/or blastogenesis of naïve and/or activated T-cells in a recipient of the pharmaceutical composition. See, e.g., FIGS. 5 to 11. Techniques to determine suppression of T-cell proliferation and blastogenesis are well known to those skilled in the art, including, for example, flow cytometry analysis.

Without being bound to any particular theory of operation, it is documented herein (FIG. 12) that the pharmaceutical compositions one or more of the anti-HLA-E monospecific monoclonal antibodies described herein (e.g., PTEG-019) are capable of augmenting production of antibodies produced by memory B cells. The antibody inducing capabilities can be applied beneficially to patients with stage III or IV of cancers, who carry memory B cells against tumor associated or tumor specific antigens but the cells remain in low numbers. Augmentation of antibodies in these patients against tumor antigens may be beneficial for such augmentation of tumor antigen antibodies are capable of targeting tumor cells and killing the tumor cells by antibody dependent cytotoxicity (ADCC) or by complement dependent cytotoxicity (CDC). In this context, one or more of carefully selected (e.g., PTEG-019) anti-HLA-E monospecific monoclonal antibodies may help to augment memory B cells as well as the antibodies per se.

Without being bound to any particular theory of operation, it is believed that of the monospecific anti-HLA-E monoclonal antibody or antibodies described herein (Table 3) can block or neutralize the pro-inflammatory or adverse effects caused by a tumor or inflammatory cell surface HLA-E or the soluble HLA-E antigen in tumor microenvironment or circulation, by interfering with the ability of the soluble HLA-E to bind to a CD+ T-lymphocyte or NKT cells-bound receptors (CD94/NKG2a) in body fluid or circulation.

In some embodiments and without being bound to any particular theory of operation, it is believed that the pharmaceutical compositions described herein can clear soluble HLA-E heavy chains from circulation.

The anti-HLA-E monospecific monoclonal antibodies described herein can function in at least two ways. Firstly, by specifically blocking HLA-E overexpressed on tumor cells as well as soluble HLA-E found in tumor microenvironment and circulation, without interfering with other cell surface or soluble HLA-I alleles. When an anti-HLA-E monospecific monoclonal antibody described herein binds to HLA-E overexpressed on tumor cells or to soluble HLA-E antigen in tumor microenvironment, it can also block or prevent the binding of HLA-E to a inhibitory receptors (CD94/NKG2a), on a CD8+ T-lymphocyte or Natural Killer T cells and their by restoring normal cytotoxic capabilities of the CD8+ T cells as well as NKT cells. Secondly, by augmenting the number of activated CD8+ T lymphocytes, the cytotoxic and anti-tumor potentials of immune cells are enhanced.

The dual functional capabilities of anti-HLA-E monospecific monoclonal antibodies described herein makes them potentially therapeutic double-edged sword against malignancy and tumor progression.

The anti-HLA-E monospecific monoclonal antibodies described herein can also expedite elimination of virally infected cells. The viral kinds include but not limited to cytomegalovirus (CMV), Epstein Barr Virus (EBV); Influenza virus, *Salmonella* enteric & *Mycobaterium* species. The anti-HLA-E monospecific monoclonal antibodies described herein can augment the number of activated CD8+ T lymphocytes and thus enhance the immune cells' cytotoxic capacity against virally infected cells. CD8+ T cell-augmentative capabilities of monospecific monoclonal antibodies is an added therapeutic benefit for virally infected patients.

Memory B cells are cells which are exposed to a foreign or self-antigen such as tumor antigen found in circulation of all humans. In cancer patients the memory cells exposed to tumor antigen remain low in number. Without being bound to any particular theory of operation, it is documented herein (FIG. 12) that one or more of the anti-HLA-E monospecific monoclonal antibodies described herein (e.g. PTEG-019) are capable of augmenting production of antibodies produced by memory B cells. The antibody inducing capabilities can be applied beneficially to patients with stage III or IV of cancers, who carry memory B cells against tumor associated or tumor specific antigens but the cells remain in low numbers. Augmentation of antibodies in these patients against tumor antigens may be beneficial for such augmentation of tumor antigen antibodies are capable of targeting tumor cells and killing the tumor cells by antibody dependent cytotoxicity (ADCC) or by complement dependent cytotoxicity (CDC). In this context, one or more of carefully selected (e.g., PTEG-019) anti-HLA-E monospecific monoclonal antibodies may help to augment memory B cells as well as the antibodies per se.

In another aspect provided herein are methods of preventing, managing, treating and/or ameliorating various diseases, the method comprising administering to a human subject a therapeutically effective amount of any one of the pharmaceutical compositions provided herein.

Studies described herein show that anti-HLA-E monospecific monoclonal antibodies can augment proliferation of CD8+ T lymphocytes. Thus, while not intending to be bound by any particular theory of operation, it is believed that pharmaceutical compositions comprising anti-HLA-E monospecific monoclonal antibodies can be used as immunomodulatory agents in preventing, managing, treating and/or ameliorating cancer and various infectious and inflammatory diseases and conditions that require greater number of activated cytotoxic CD8+ T lymphocytes.

Studies described herein show that anti-HLA-E monospecific monoclonal antibodies can augment memory B cells and their unique antibodies. Thus, while not intending to be bound by any particular theory of operation, it is believed that pharmaceutical compositions comprising anti-HLA-E monospecific monoclonal antibodies can be used as selective antibody producing agents in preventing, managing, treating and/or ameliorating cancer and various infectious and inflammatory diseases and conditions that require antibodies against host's own antigens or pathogens, including but not limited to viruses and bacteria.

A therapeutically effective amount of the pharmaceutical composition is an amount that is required to reduce the severity, the duration and/or the symptoms of a particular disease or condition. The amount of a pharmaceutical composition that will be therapeutically effective in the prevention, management, treatment and/or amelioration of a particular disease can be determined by standard clinical techniques. The precise amount of the pharmaceutical composition to be administered with depend, in part, on the route of administration, the seriousness of the particular disease or condition, and should be decided according to the judgment of the practitioner and each human patient's circumstances. Effective amounts may be extrapolated from dose-response curves derived from preclinical protocols either in vitro using T-cells from patients as illustrated in FIGS. 5 to 11 or using in vivo animal (e.g., Wistar or Lewis rat or different strains of mice used for different diseases, or Cynomolgous monkey) test systems.

In some embodiments, the effective amount of an antibody of the pharmaceutical composition provided herein is between about 0.025 mg/kg and about 1000 mg/kg body weight of a human subject. In certain embodiments, the pharmaceutical composition is administered to a human subject at an amount of about 1000 mg/kg body weight or less, about 950 mg/kg body weight or less, about 900 mg/kg body weight or less, about 850 mg/kg body weight or less, about 800 mg/kg body weight or less, about 750 mg/kg body weight or less, about 700 mg/kg body weight or less, about 650 mg/kg body weight or less, about 600 mg/kg body weight or less, about 550 mg/kg body weight or less, about 500 mg/kg body weight or less, about 450 mg/kg body weight or less, about 400 mg/kg body weight or less, about 350 mg/kg body weight or less, about 300 mg/kg body weight or less, about 250 mg/kg body weight or less, about 200 mg/kg body weight or less, about 150 mg/kg body weight or less, about 100 mg/kg body weight or less, about 95 mg/kg body weight or less, about 90 mg/kg body weight or less, about 85 mg/kg body weight or less, about 80 mg/kg body weight or less, about 75 mg/kg body weight or less, about 70 mg/kg body weight or less, or about 65 mg/kg body weight or less.

In some embodiments, the effective amount of an antibody of the pharmaceutical composition provided herein is between about 0.025 mg/kg and about 60 mg/kg body weight of a human subject. In some embodiments, the effective amount of an antibody of the pharmaceutical composition provided herein is about 0.025 mg/kg or less, about 0.05 mg/kg or less, about 0.10 mg/kg or less, about 0.20 mg/kg or less, about 0.40 mg/kg or less, about 0.80 mg/kg or less, about 1.0 mg/kg or less, about 1.5 mg/kg or less, about 3 mg/kg or less, about 5 mg/kg or less, about 10 mg/kg or less, about 15 mg/kg or less, about 20 mg/kg or less, about 25 mg/kg or less, about 30 mg/kg or less, about 35 mg/kg or less, about 40 mg/kg or less, about 45 mg/kg or less, about 50 mg/kg or about 60 mg/kg or less.

In some embodiments, the method further comprises co-administering to the human subject one or more immunomodulatory agents with the pharmaceutical composition. Examples of immunosuppressive agents that can be co-administered with the pharmaceutical composition include, but are not limited to corticosteroids, vitamin D3, Zinc, Calcium, Magnecium Selenium or selenites, azathioprine, prednisone, cylcosporin, cyclophosphamide, OKT3, FK506, mycophenolic acid or the morpholmethylester thereof, 15-deoxyspergualin, rapamycin, mizoribine, misoprostol, anti-interleukin-1 receptor antibodies, an anti-lymphocyte globulin, Velcade, Bortesomib, inhibitors of plasma cells and antibody production, NFκB, MERK, Akt, Jun pathway inhibitors, and phytonutrients or plant chemical nutrients, such as carotenoids (alpha-carotene, beta-carotene, lycopene, lutein, zeaxanthin, and cryptoxanthin), capsaisin, coumarins, flavanoids, flavonolignans, xilibinin or mixture of silymarin (silibinin A and B, isosibilinin A and B, silicristin, silidianin), ellagic acid, isoflavones, isothiocyanates, lignans, polyphenols (e.g., epicatechins-EC, epicatechin gallate-ECG, epigallocatechin-EGC, epigallocatechin gallate, EGCG, oxidized quinonoids, curcuminoids, curcumin), saponins and phytosterols and multiminerals including but not limited to Zinc, Calcium, Magnecium Selenium or selenites, The pharmaceutical composition of the method can be administered using any method known to those skilled in the art. For example, the pharmaceutical composition can be administered intramuscularly, intradermally, intraperitoneally, intravenously, subcutaneously administration, or any combination thereof. In some embodiments, the pharmaceutical composition is administered subcutaneously. In some embodiments, the composition is administered intravenously. In some embodiments, the composition is administered intramuscularly.

6. EXAMPLES

The following examples are presented to further document the supporting evidences and aspects of the compositions and describe the methods provided herein. Example 1 provides development and characterization of monospecificity of anti-HLA-E monoclonal antibodies and their potency and reliability for immunodiagnostic application. This example also shows that several anti-HLA-E monoclonal antibodies are immunoreactive only with HLA-E but not immunoreactive to HLA-A, HLA-B, HLA-Cw, HLA-F and HLA-G. Example 2 shows the therapeutic relevance of the HLA-E-monospecific monoclonal antibodies for blocking tumor cell surface HLA-E from binding to CD94/NKG2a inhibitory receptors on CD8+ T lymphocytes and NKT cells. Example 3 shows the therapeutic relevance of the HLA-E-monospecific monoclonal antibodies in augmenting the production of CD8+ cytotoxic T-lymphoblasts needed for tumor killing. This example also shows that HLA-E monospecific monoclonal antibodies are capable of activating CD8+ T lymphoblasts and naïve Cells even in the absence of phytohemagglutinin (PHA-L), which is capable of stimulating human T lymphocytes and inducing blastogenesis. Example 4: shows the therapeutic relevance of the HLA-E-monospecific monoclonal antibodies in augmenting the production of antibodies by isolated memory B cells in circulation. This example provides scope for extending the use of the HLA-E monospecific monoclonal antibodies for augmenting the production of antibodies against tumor antigens such that these antibodies can kill tumor cells by antibody dependent cytotoxicity (ADCC) and/or complement-dependent cytotoxicity (CDC).

Example 1

Determination of Monospecificity of Anti-HLA-E Monoclonal Antibodies and their Potency and Reliability for Immunodiagnostic Application Five of the twenty-four HLA-E-monospecific monoclonal antibodies are used here as examples. These anti-HLA-E monospecific monoclonal antibodies (mAbs) were generated after immunizing BALB/c mice with recombinant heavy chains of two alleles of HLA-E: HLA-$E^R$ and HLA-$E^G$. The two alleles differ at position 107 of the HLA-E heavy chain: HLA-$E^R$ has a glycine (G) and HLA-$E^G$ has an Arginine(R). Clone Nos 1-258 were subject to analysis. Monospecificity of monoclonal anti-HLA-E antibodies is critical for reliable assessment of HLA-E overexpression in tumor cells or inflamed tissues. At present, almost all the clinical diagnosis of HLA-E in human cancers are carried out with one or more of the commercially available monoclonal antibodies, namely MEM-E/02, MEM-E/06, MEM-E/07, MEM-E/08 and 3D12 were cross reactive to HLA-A, HLA-B, HLA-Cw, a pair of each of these alleles are found in every human tissue, including human cancer cells. Not only these anti-HLA-E antibodies bind to these HLA-Ia antigens, some of the antibodies considered to be useful for monitoring HLA-Ia antigens such as mAb W6/32 and mAb HC10 also bind to HLA-E (see details in Ravindranath et al. 2010a, 2011). The present example demonstrates that HLA-E monospecific monoclonal antibodies (n=24) are immunoreactive only to HLA-E but not immunoreactive to HLA-A, HLA-B, HLA-Cw, HLA-F and HLA-G (Table 3). Hence, the monoclonal antibodies described herein are referred to as HLA-E monospecific. After examining the immunoreactivity of the antibody secretions of the 258 hybridoma clones, obtained after immunization of HLA-$E^{R107}$ and HLA-$E^{G107}$, it is discovered that 24 monoclonal antibodies from 24 hybridoma clones are monospecific in that it uniquely reacted only with HLA-E.

A multiplex Luminex®-based immunoassay was used to determine the immunoreactivity of the antibody secretions from 258 hybridoma clones against HLA-E and HLA-A, HLA-B, HLA-Cw, HLA-F and HLA-G. The mean fluorescent intensity of the antibodies reacting to HLA-E and HLA-A, HLA-B, HLA-cw, HLA-F and HLA-G were determined initially. After selecting and regrouping the monospecific monoclonal antibodies of culture supernatants, the mAbs were selected for inhibition experiments with peptide epitope amino acid sequences found only on HLA-E heavy chain polypeptide but not present on the heavy chain polypeptides of HLA-A, HLA-B, HLA-Cw, HLA-F and HLA-G (Table 2). After ascertaining monospecificity of the monoclonal antibodies by peptide inhibition with specific peptide sequences (FIG. 4), the culture supernatants were further processed to compare the intensity of immunoreactivity of culture supernatants before and after passing through the Protein G column, that of the eluates before and after concentration (FIG. 2). Using concentrated Protein-G eluates of the selected monospecific monoclonal antibodies, the potency was determining by ascertaining the titers of the monoclonal antibodies after titration by serial dilution not and their Protein-G eluates before and after concentration (FIG. 3). The titer values can be used to grade the TFL monoclonal antibodies for immunodiagnosis.

Principles of dual-laser flow cytometric protocols of Luminex® xMAP® multiplex technology, the single Ag (allele) assays were carried out for data acquisition and quantitative (Mean Florescent Intensity or MFI) estimation of the level of HLA-E Abs. The Luminex® assays utilize microbeads on which individual HLA Ags (HLA-E and HLA Ia antigens) have been covalently bonded (xMap® assays). XMap® microbeads contain two reporter fluorophores that are proportionally varied to identify them as one of 100 possible bead identifiers. The recombinant HLA antigens were attached to 5.6 g polystyrene microspheres by a process of simple chemical coupling, the microspheres internally dyed at One Lambda with red and infrared fluorophores, using different intensities of two dyes (xMAP® microsphere number #005). The LABScreen® (One Lambda, Canoga Park, Calif.) consists of a panel of color-coded microspheres (SAB, coated with single Ag HLA alleles) to identify Ab specificities. The array of HLA Ags representing various alleles on the beads are listed at the One Lambda website under Ab detection products/LABScreen® Single Ag Product sheet/HLA Ia combi-LS1A04-Lot 002 Worksheet Rev-1. The SAB products in LS1A04 include 31 HLA-A, 50 HLA-B and 16 HLA-C alleles. It should be noted that not all existing HLA Ia alleles are represented in the beads analyzed.

Three kinds of beads were used: (1) negative control beads that do not contain any proteins; (2) positive control beads coated with human Immunoglobulin (Ig), most commonly IgG; and (3) experimental beads coated with HLA-E or HLA Ia alleles. The recombinant HLA antigens were attached to 5.6µ polystyrene microspheres by a process of simple chemical coupling, the microspheres internally dyed at One Lambda with red and infrared fluorophores, using different intensities of two dyes (xMAP® microsphere number #005). Using dual-laser flow cytometric principles of Luminex® xMAP® multiplex technology, the single Ag (allele) assays were carried out for data acquisition and quantitative estimation of the level of HLA-E Abs. The Luminex® assays utilize microbeads on which individual HLA Ags have been covalently bonded (xMap® assays). XMap® microbeads contain two reporter fluorophores that are proportionally varied to identify them as one of 100 possible bead identifiers. The LABScreen® (One Lambda, Canoga Park, Calif.) consists of a panel of color-coded microspheres (SAB, coated with single Ag HLA alleles) to identify Ab specificities. The array of HLA Ags representing various alleles on the beads are listed at the One Lambda website under Ab detection products/LABScreen® Single Ag Product sheet/HLA Ia combi-LS1A04-Lot 002 or LS1A04-Lot 005 Worksheet Rev-1. The SAB products in LS1A04 include 31 HLA-A, 50 HLA-B and 16 HLA-C alleles. It should be noted that not all existing HLA Ia alleles are represented in the beads analyzed. The recombinant HLA-E heavy chain was attached to 5.6 micron polystyrene microspheres by a process of simple chemical coupling, the microspheres internally dyed at One Lambda with red and infrared fluorophores, using different intensities of two dyes (xMAP® microsphere number #005). Recombinant HLA-E folded heavy chain (10 mg/ml in MES buffer) was purchased from the core facility at the Immune Monitoring Lab., Fred Hutchinson Cancer Research Center, University of Washington, Seattle, Wash. Data generated with Luminex® Multiplex Flow Cytometry (LABScan® 100) were analyzed using computer software. PE-conjugated anti-Human IgG Abs were used for the immunolocalization of the Ab bound to Ags coated on to the microbeads. The reporter fluorophore intensity was then measured in a specialized flow cytometer together with the microbead identifiers, and the fluorescence measurement was classified by bead identifier. Florescence intensity from a sample of 90 or more beads was collected. The Trimmed Mean was obtained by trimming a percent off the high and low ends of a distribution and finding the mean of the remaining distribution.

Table 3 provides the list of HLA-E monospecific monoclonal antibodies and their isotypes. Of the 258 clones developed, only 24 of them produced antibodies monospecific of HLA-E as indicated by the mean fluorescent intensities for HLA-E, HLA-F, HLA-G, HLA-A, HLA-B and HLA-Cw. The MFI of the culture supernatants of different mAbs varied very much and they are listed in the table. PTER-033, PTER-034, PTER-073, PTER-074 & PTER-145 were selected to study their potential for immunodiagnosis and for immunomodulation studies reported herein.

Comparing the amino acid sequences of the heavy chain polypeptides of HLA-E, HLA-F, HLA-G, HLA-A, HLA-B and HLA-Cw, the peptides sequences monospecific for HLA-E were identified particularly in α1 and α2 helices of HLA-E heavy chain of both the HLA-E alleles (HLA-$E^{R107}$ and HLA-$E^{G107}$). Table 2 reveals the peptide sequences or epitopes specific only for HLA-E, a critical determinant that encouraged the search for anti-HLA-E monospecific monoclonal antibody for diagnostic purposes, since the currently available commercial ant-HLA-E mAbs show tremendous HLA-Ia reactivity (Ravindranath et al., 2010a and 2011) HLA-E specific epitopes shed light on the unique functional capabilities of HLA-E and the nature of antibodies that may bind to these epitopes, which are not only important for specific immunodiagnosis of the HLA-E in malignant and inflamed tissues but also to unravel their specific immunomodulatory efficacy. Amino acids in the α1 and α2 helices are important since they are involved in functions related to antigen presentation and binding to inhibitory or activating ligands on other immune cells including CD8+ T cells and NKT cells.

After identifying the unique peptide sequences of HLA-E, the peptides were chemically synthesized and tested for inhibitory potential of anti-HLA-E monospecific monoclonal antibodies. FIG. 4 illustrates dosimetric inhibition of the HLA-E monospecific monoclonal antibody PTER-033 with HLA-E peptide epitope sequence at varying concentrations. The linear dosimetric inhibition confirms that the epitope located in α2 helix may be specific domain recognized by PTER-033 than that located in α1 helix.

FIG. 3 illustrates the profiles emerging from the titration (after serial reciprocal dilutions) of HLA-E reactivity (expressed as Trimmed Mean Florescent Intensity) of concentrated Protein-G purified eluates of the monospecific anti-HLA-E antibodies (PTER-033, PTER-034, PTER-073, PTER-074 & PTER0145). MFI 1000 is used to determine the titer (which reflects the potency) of different monoclonal antibodies. Based on the estimates the titers of different antibodies can be ranked as follows: PTER-034 [200], PTER-074 [300], PTER-073 [500], PTER-033 [1000] & PTER-145 [>5000]. The concentration of the monoclonal used is indicated at 1/10 dilution in ng. Both the titer values and protein concentration of the mAbs are valuable for developing potential HLA-E monospecific immunodiagnostic reagents.

The proof of principle of the potential usefulness for monitoring cell surface expression of HLA-E in tumor tissues with highly (both titer and concentration of the protein are considered) monospecific monoclonal anti-HLA-E antibodies is documented herein. FIG. 5 documents specific immunostaining of HLA-E expressed on tumor cells with anti-HLA-E mAb. Culture supernatants of the monospecific HLA-E antibodies (PTER-033, PTER-034, PTER-073, PTER-074, PTER-145) were used at V2 dilution. MEM-E/02, a HLA-E non-specific commercially concentrated mAb (reacts with several HLA-Ia alleles). Note the non-specific and background staining by MEM-E/02 and clear specific staining with the monospecific HLA-E monoclonal antibodies. Staining with the mAbs are reliable because of the HLA-E-monospecificity of the monoclonal antibodies. Serial paraffin sections of tumor biopsies of Melanoma (AJCC Stage II; T2NOMO) surgically resected from left arm of 75 yr female was used for immunodiagnosis.

Example 2

Therapeutic Relevance of the HLA-E-monospecific Monoclonal Antibodies: For Blocking Tumor Cell Surface HLA-E from Binding to CD94/NKG2a Inhibitory Receptors on CD8+ T Lymphocytes and NKT Cells Different kinds of cancers and their cells overexpress HLA-E. Upon tumorigenesis, CD8+ cytotoxic T cells enter into tumor tissues and kill tumor cells by releasing factors inducing cell death (both apoptosis and necrosis). However, tumor cells escape the attack of CD8+ T-lymphocytes by inducing overexpression of HLA-E. Previous literature point out that cytokines primarily IFN-γ released by infiltrating lymphocytes augment the expression of HLA-E. When HLA-E is overexpressed on cancer cells, the HLA-E molecules bind to CD94 and NKG2a receptors on CD8+ T cells and NKT cells, the inhibiting receptor CD94/NKG2A dampens the incoming activation signals of T cells by recruitment of phosphatases like SHP-1 to the signal transducing synapse, resulting in decreased effector function.

FIGS. 1A and 1B illustrate the precise domain of α1 and α2 helices of HLA-E that binds to CD94 and NKG2a receptors on CD8+ T cells and NKT cells. It is important to identify the amino acids in α1 and α2 helices of HLA-E that bind with CD94 epitope and NKG2a epitopes. This example demonstrates that two of the peptide sequences that are specific for HLA-E and recognized by HLA-E monospecific monoclonal antibodies express the specific amino acids that bind to CD94 and NKG2a. Note that amino acids in HLA-E α1 helix bind to CD94, while α2 helix amino acids bind to NKG2a. Most importantly these amino acids in HLA-E α1 and α2 helices are recognized by the monospecific HLA-E monoclonal antibodies. The figure clearly illustrates the epitopes recognized by monospecific HLA-E- mAbs and CD94/NKG2a receptors.

Table 2 provides the peptide sequences or epitopes specific ($^{65}$RSARDTA$^{71}$ (SEQ ID NO:3) and $^{143}$SEQKSNDASE$^{152}$ (SEQ ID NO:11)) for HLA-E and those shared between HLA-E and HLA class Ia. These HLA-E restricted epitopes may vary in length, while carrying the amino acids that are involved in ligand-receptor interaction with CD94/NKG2a. Amino acids in the α1 and α2 helices are important since they are involved in functions related to antigen presentation and binding to inhibitory or activating ligands on other immune cells including CD8+ T cells and NKT cells. Table 2 lists the peptide sequences or epitopes specific only for HLA-E, a critical determinant that encouraged the search for anti-HLA-E monospecific monoclonal antibody for diagnostic purposes. Any monoclonal antibody that specifically recognizes one or more amino acids that bind to CD94/NKG2a would sufficient for blocking HLA-E interaction with the receptors. Their binding to the site of the ligand that interacts with receptor can create stearic hindrance for the HLA-E ligands to interact with CD94/NKG2a.

This example also illustrates that the amino acid sequences of these epitopes ($^{65}$RSARDTA$^{71}$ (SEQ ID NO:3) and $^{143}$SEQKSNDASE$^{152}$ (SEQ ID NO:11)), that are also involved in binding to CD94/NKG2a inhibitory receptors on CD8+ T cells and NKT cells, are capable of specifically inhibiting the binding of HLA-E-specific mAbs to HLA-E. FIG. 4 documents the dosimetric inhibition of a HLA-E-monospecific monoclonal antibody PTER-033 with HLA-E peptide epitope sequences ($^{65}$RSARDTA$^{71}$ (SEQ ID NO:3) and $^{143}$SEQKSNDASE$^{152}$ (SEQ ID NO:11)) at varying concentrations.

For assessment of specific recognition of the HLA-E specific peptides of HLA-E monospecific monoclonal antibodies, dosimetric peptide inhibition studies were carried out. For experiments, three sets of antibodies were used. One set of antibodies were exposed to different dilutions peptide #1 ($^{65}$RSARDTA$^{71}$ (SEQ ID NO:3)) for known concentration of mAb for 1 hr at room temperature (RT), second set of antibodies were exposed different dilutions of peptide #2 ($^{143}$SEQKSNDASE$^{152}$ (SEQ ID NO:11))for known concentration of mAb for 1 hr at RT. Third set consists of mAb not treated with peptides. Mean Fluorescent intensities were obtained after treatment. Three kinds of beads were used: (1) negative control beads that do not contain any proteins; (2) positive control beads coated with human Immunoglobulin (Ig), most commonly IgG; and (3) experimental beads coated with HLA-E or HLA Ia alleles. Recombinant HLA-E folded heavy chain (10 mg/ml in MES buffer) was purchased from the core facility at the Immune Monitoring Lab., Fred Hutchinson Cancer Research Center, University of Washington, Seattle, WA. The recombinant HLA-E was attached to 5.6 µ polystyrene microspheres by a process of simple chemical coupling, the microspheres internally dyed at One Lambda with red and infrared fluorophores with red and infrared fluorophores, using different intensities of two dyes (xMAP® microsphere number #005). Using dual-laser flow cytometric principles of Luminex® xMAP® multiplex technology, the single Ag (allele) assays were carried out for data acquisition and quantitative estimation of the level of HLA-E Abs. Data generated with Luminex® Multiplex Flow Cytometry (LABScan® 100) were analyzed using computer software. PE-conjugated anti-Human IgG Abs were used for the immunolocalization of the Ab bound to Ags coated on to the microbeads. The reporter fluorophore intensity was then measured in a specialized flow cytometer together with the microbead identifiers, and the fluorescence measurement was classified by bead identifier. Florescence intensity from a sample of 90 or more beads was collected. The Trimmed Mean was obtained by trimming a percent off the high and low ends of a distribution and finding the mean of the remaining distribution. The results are illustrated in FIG. 4.

Example 3

Therapeutic Relevance of the HLA-E-monospecific Monoclonal Antibodies: Promoting Production of CD8+ Cytotoxic T-lymphoblasts Needed for Tumor Killing This example provides strategies to increase CTL numbers with HLA-E monospecific monoclonal antibodies.

This example depicts the activation of T-lymphocytes with HLA-E monospecific monoclonal antibodies with or without using a lectin Phytohemagglutinin (PHA-L), which is capable of stimulating human T-lymphocytes and inducing blastogenesis. PHA-L stimulated T-lymphocytes and PHA-untreated T-lymphocytes ere used to test the ability of few HLA-E monospecific monoclonal antibodies and the claimed antibodies provided herein to promote proliferation and blastogenesis CD8+ cytotoxic T lymphocytes.

Events occurring 72 hrs after exposure of PHA-L or no PHA on CD4−/CD8+, CD4+/CD8−, CD4+/CD8+ and CD4−/CD8− T-lymphocytes (CD3+) were assessed using whole blood (20 ml) drawn from a healthy donors into Acid Citrate Dextrose (ACD) tubes. Whole blood (15 ml) was pipetted into 25 ml of PBS (without calcium or magnesium) in a 50 ml conical centrifuge tube and underlayed with Ficoll-Hypaque (10 ml) at room temperature. After centrifugation (20 min. at 800 g (2000 rpm in H-1000 rotor), 20° C.)), the plasma-platelet-containing supernatant was aspirated from above the interface band. The interface band, which includes the lymphocytes, was then aspirated with <5 ml of fluid and transferred to a new 50 ml centrifuge tube, combining the bands from 2 to 3 Ficoll-Hypaque gradients. PBS was then added to the combined interface bands to a total volume of 50 ml and centrifuged (10 min. at 600 g (1500 rpm in H-1000 rotor), 20° C.). The supernatants were aspirated and the pellet in each tube was combined and resuspended in 10 ml of PBS at RT. PBS was then added to a volume of 50 ml and the mixture was centrifuged (15 min. 300 g (750 rpm in H-1000 rotor), 20° C.). The lymphocyte pellet was resuspended in PBS (1 ml) at RT and the viable cells were counted. The cells were then distributed equally among three Fisher tubes with PBS and centrifuged (1 min. at 1000 g). The supernatant was discarded and the pellet was re-suspended and mixed well with 0.8 ml of Lympho-Kwik® T. The mixture was incubated (20 min. at 37° C. or RT) in a water bath or heat block with occasional mixing by inverting capped tube. PBS (0.2 ml) was then layered over the cell preparation and centrifuged (2 min. at 2000 g). The pellet was resuspended in PBS and centrifuged (1 min. at 1000 g). Washing was repeated once and each pellet was resuspended in 0.8 ml of the following Lympho-Kwik® T Prep. The entire mixing, incubation, centrifugation and resuspension of pellet was repeated. In the final step, the pellet was resuspended in AIM-V medium+1% HEPES at a final concentration of $5 \times 10^7$ cells/ml. An aliquot was tested for purity of T-cells using CD3 monoclonal antibody in flow cytometry. The cells were labeled with CFSE. The quantity of cells labeled was $10^5$ to $10^6$ cells per ml 10% heparinized donor plasma added. Two microliters of 5 mM CFSE per milliliter cells (final 10 µM) was added into a tube that was ≥6× the volume of cells. The cells were incubated (15 min. at RT or for 10 min. at 37° C.). The staining was quenched by adding 5 vol ice-cold. AIM-V medium (+1% HEPES buffer, with 10% heparinized plasma from donor) and the cells were incubated on ice for 5 min. The cells were washed three times in the culture medium to ensure that CFSE bound to protein in the supernatant was removed, preventing any subsequent uptake into bystander cells.

The in vitro cell culture assays were set up in 96 well tissue culture plates. Purified PHA-L was added to specific wells at a concentration of 1.12 µg/ml. The final cell concentration was 2×105 cells/well. Negative and positive controls were run in triplicates. For negative controls, 10 µl of CFSE labeled cells (2×105 cells) were added to wells containing 190 µl of AIM-V. For positive controls, 10 µl of CFSE labeled cells (2×105 cells in 100 µl/well) were added to wells containing 90 µl of PHA-L in AIM-V and 100 µl of AIM-V. One of the three profiles of the controls is presented in FIG. 5.

Two monoclonal antibodies were used: (1) CD8 MAb is indicated by the Y or vertical axis; and (2) CD4 MAb is indicated by the X or horizontal axis. Upper left quadrant: CD8 positive cells; lower left quadrant: CD8 negative cells; upper right quadrant: CD8 positive and CD4 positive T-lymphocytes; lower right quadrant: CD8 negative and CD4 negative cells. Cells, in the left most quadrants were CD8+/CD4+ primordial T-cells or even include dead cells. Cells stained red in the middle quadrants were CD8+/CD4+ naïve T-cells but may also include a minor component of activated T-cells. Cells in the right quadrants were CD8+/CD4+ T-lymphoblasts. Lymphoblasts were identified by the size of the cells which results in migration of the cells towards left or upper side, indicative of the increased size and possibly granulation. Table 4 compares proliferation of T cells after exposure of different HLA-E monospecific monoclonal antibodies in PHA negative (after 72 hrs) wells with PHA positive (after 72 hrs) wells. What is most striking is that CD8+ T lymphoblast not only increase significantly in number after exposure to the monoclonal antibodies in PHA positive wells but also more strikingly and significantly in PHA negative wells. This critical finding points out that HLA-E monospecific monoclonal antibody per se is capable of activating the number of Cytotoxic CD8+ T cells (CTLs) even without PHA. In fact increase observed after PHA exposure is not much better than that observed without PHA exposure. This experiment was done in triplicate and Table 4 is representative of the findings.

Table 4 compares the effects of different exemplary monospecific HLA-E monoclonal antibodies (PTER-033, PTER-034, PTER-073, PTER-074 & PTER-145) at two different concentrations or dilutions in the presence or absence of PHA) on CD4−/CD8+, CD4+/CD8−, CD4+/CD+ and CD4−/CD8− T-lymphoblasts and CD4−/CD8+, CD4+/CD8−, naïve T cells. The effects of exemplary monospecific HLA-E monoclonal antibodies are also compared with an exemplary nonspecific HLA-E monoclonal antibody (PTER-007). Note that stimulation or activation of CD8+ T lymphoblasts occur even without PHA suggesting the proliferative potential of the exemplary HLA-E monospecific monoclonal antibody. Also, note that mAb potentially useful for immunodiagnosis (PTER-145) is not potential immunomodulator, whereas PTER-033 and PTER-034 are potential generators of CD8+ T-lymphoblasts. In the absence of PHA, these mAbs do not influence CD4+/CD8− or CD4+/CD8+ T cells. However, total number of lymphocytes was invariably augmented by mAbs PTER-033 and PTER-034 both in the presence and in the absence of PHA. Stimulation of CD8+ naïve T cells are also observed with HLA-E specific mAb, however it was significant only for PTER-034 and PTER-145 at specific dilutions.

FIG. 6 shows the number of activated CD8+ T-lymphoblasts after exposure to monospecific HLA-E monoclonal antibody PTER-033 at two different concentrations or dilutions (1/30 & 1/150) in the presence or absence of PHA. Note that stimulation or activation of CD8+ T lymphocytes occur even without PHA suggesting the immunomodulatory potential of the exemplary monospecific HLA-E monoclonal antibody.

FIG. 7 shows the number of activated CD8+ T-lymphoblasts after exposure to exemplary monospecific HLA-E monoclonal antibody PTER-034 at two different concentrations or dilutions (1/10 & 1/50) in the presence or absence of PHA. Note that stimulation or activation of CD8+ T lymphocytes occur even without PHA suggesting the immunomodulatory potential of the exemplary monospecific HLA-E monoclonal antibody.

Figure 1B:
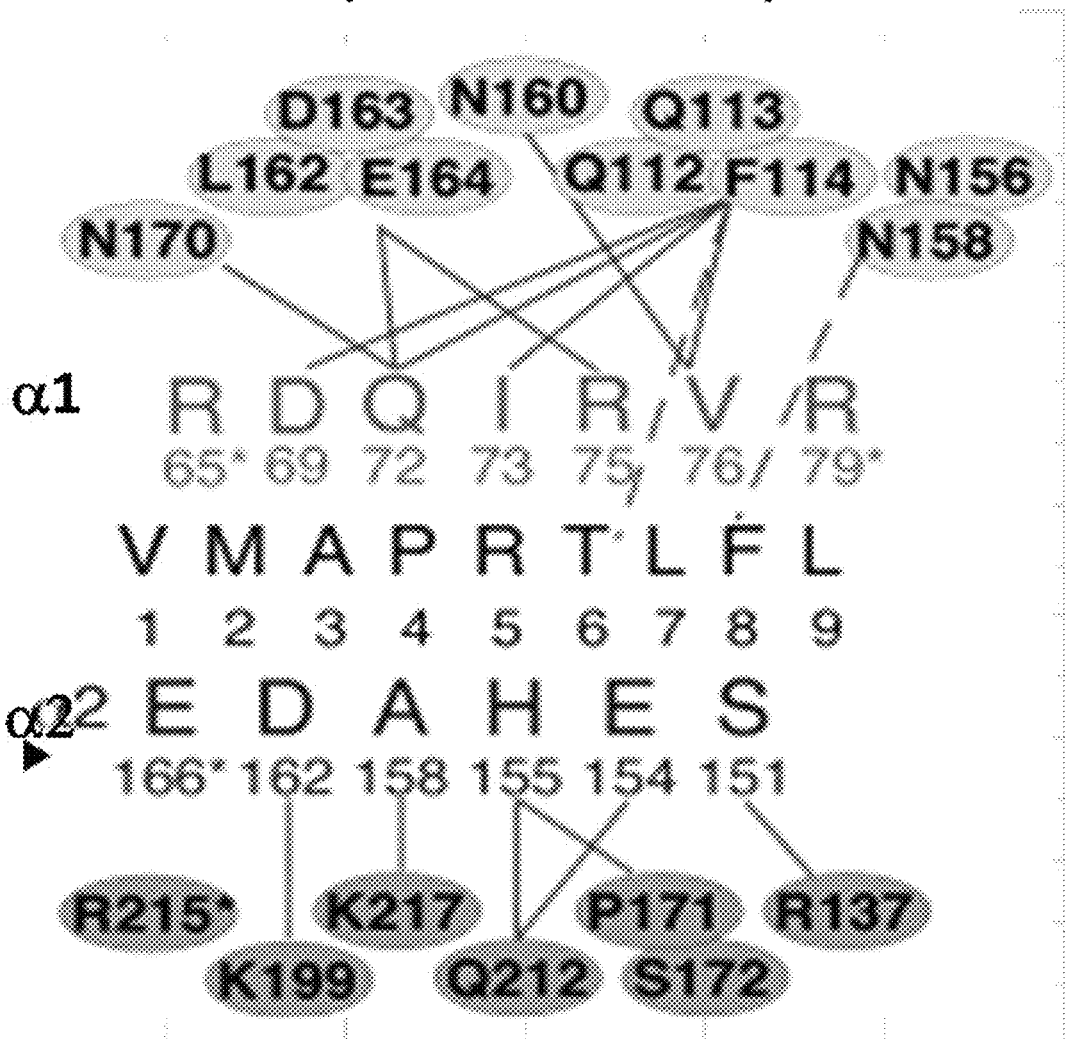
Figure 2:
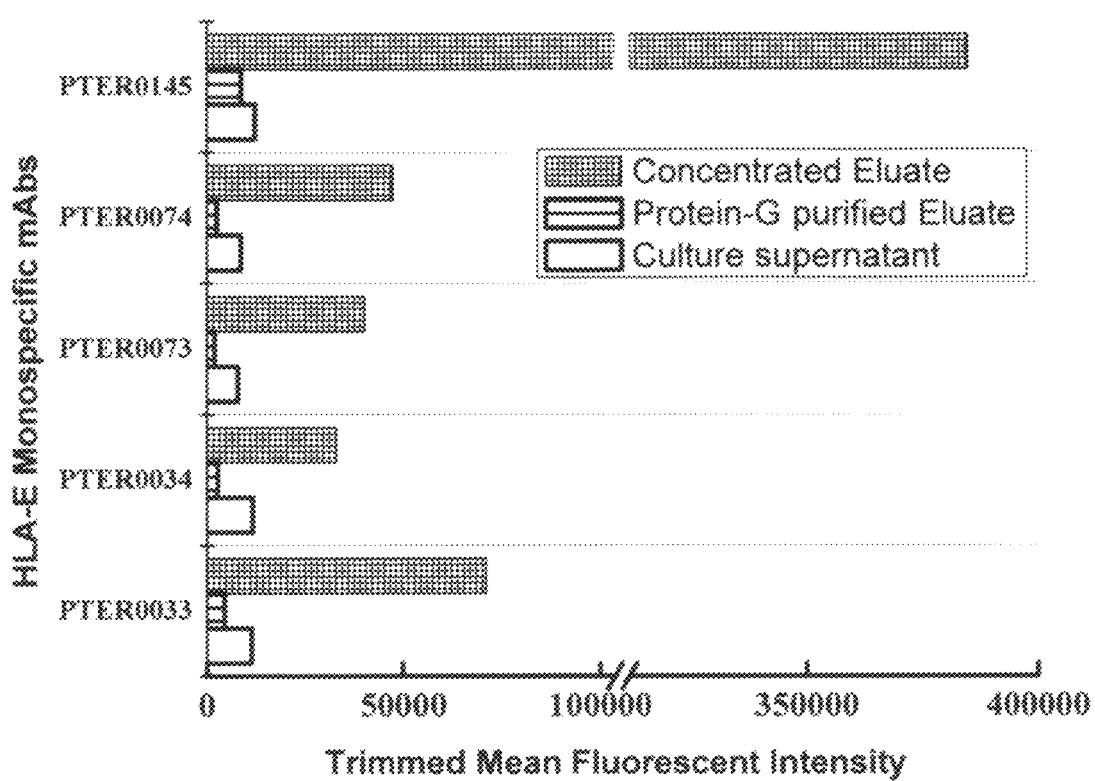
Figure 3:
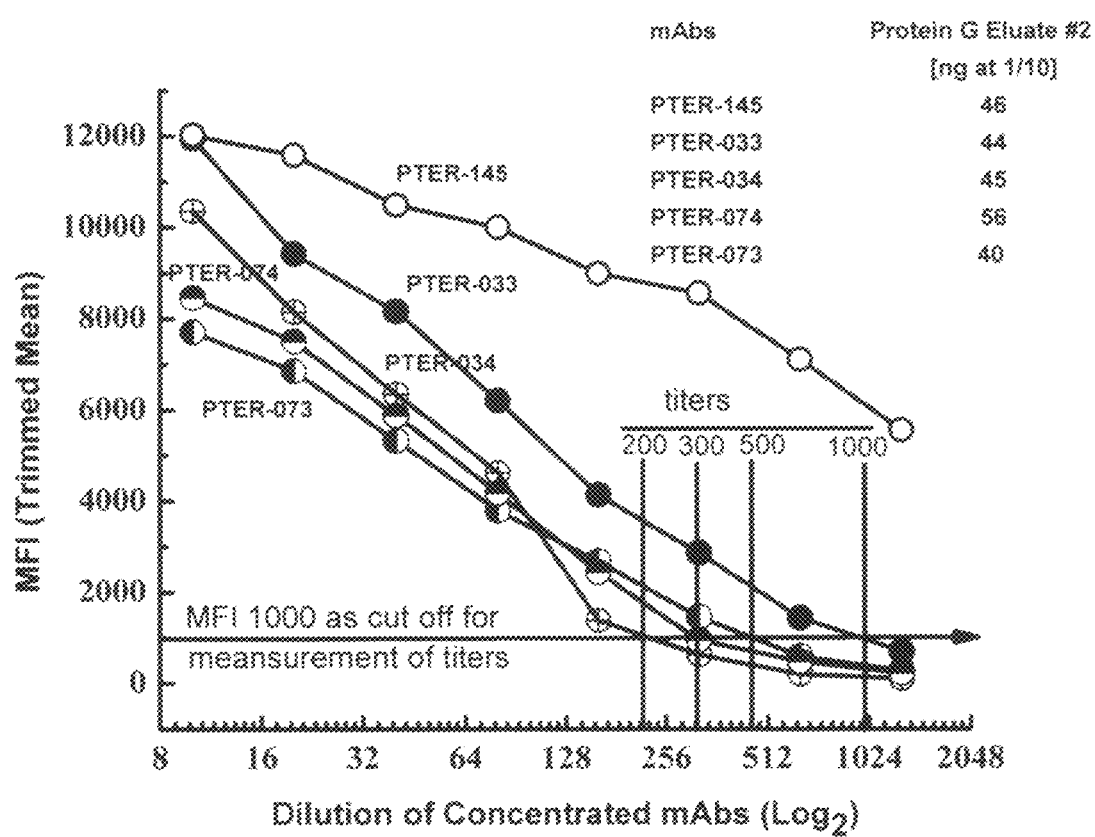
Figure 4:
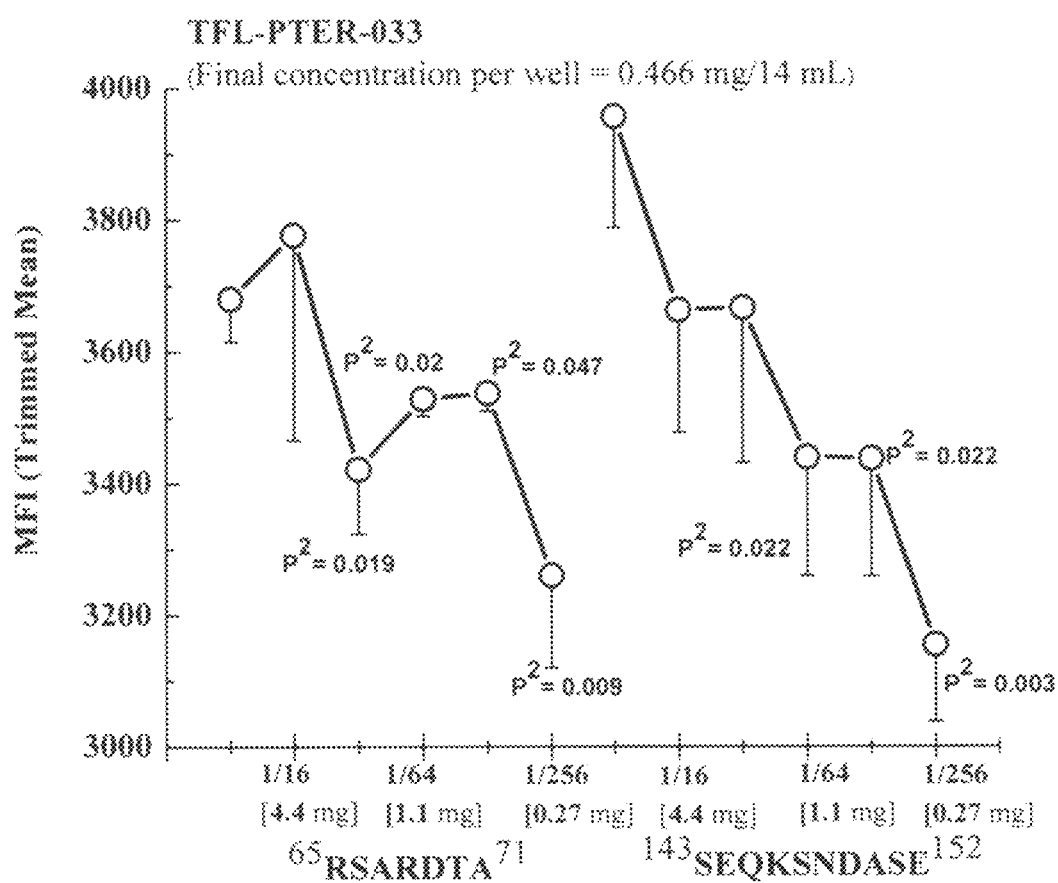
Figure 5:
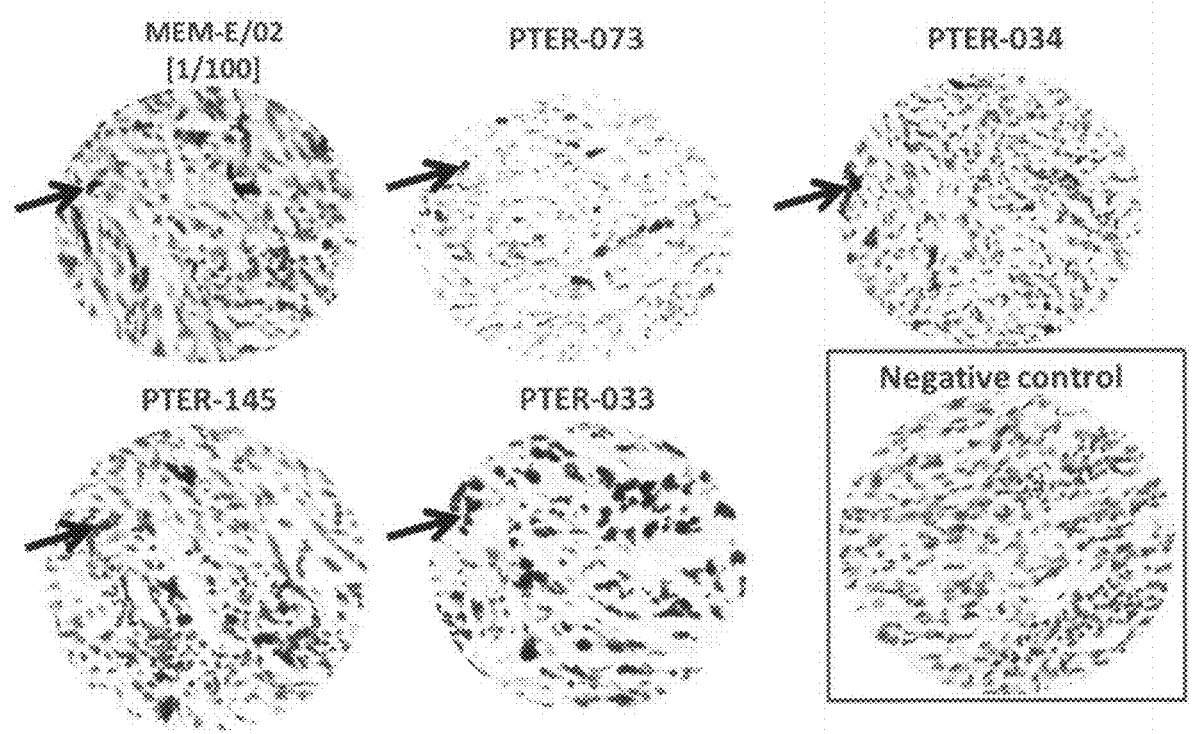
Figure 6:
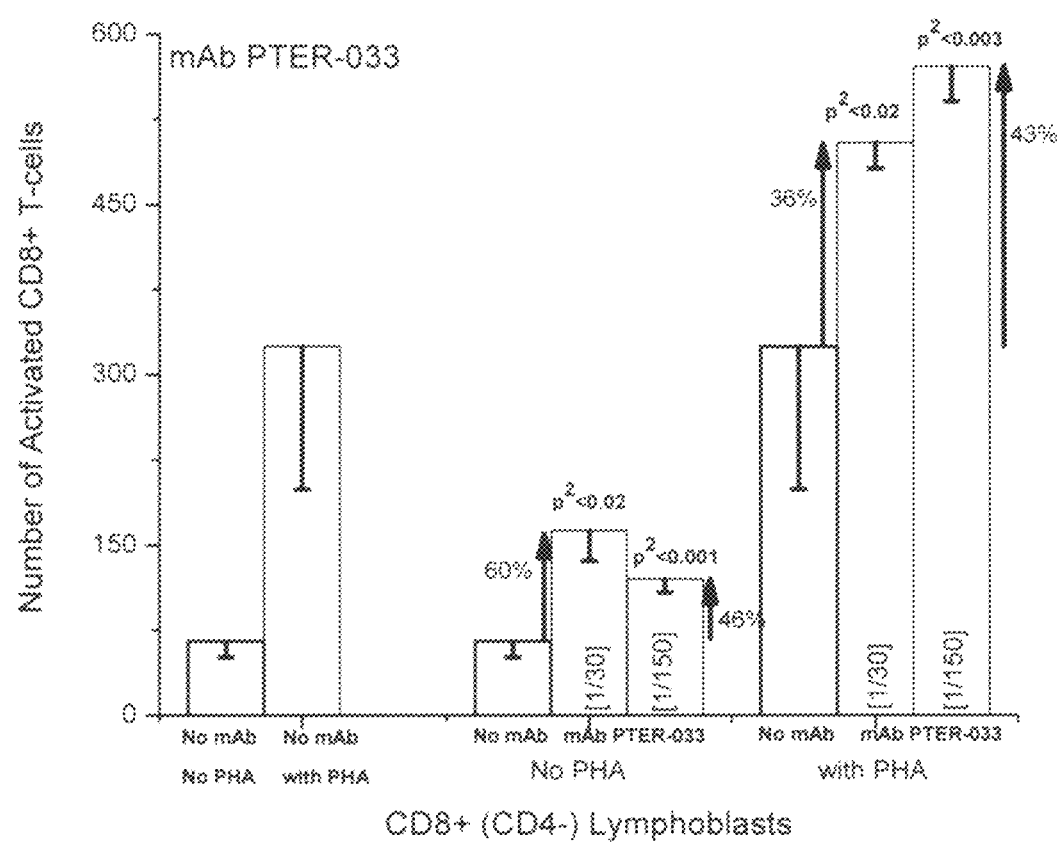
Figure 7:
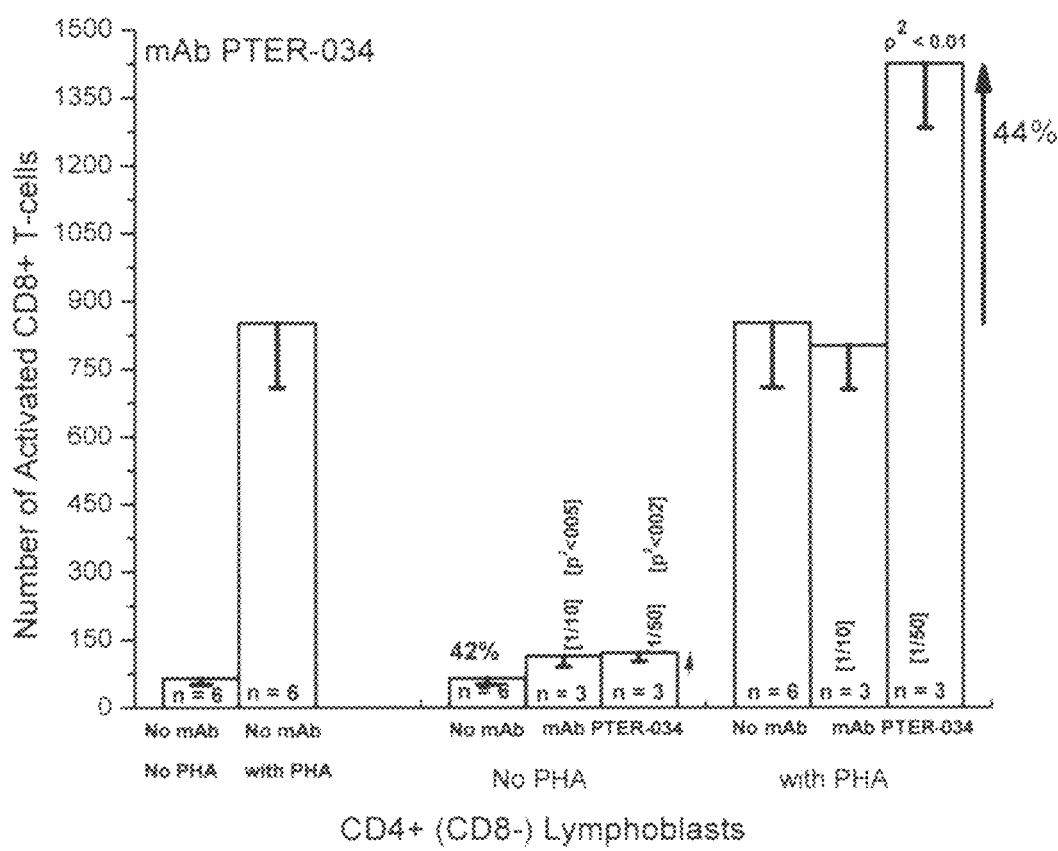
Figure 8:
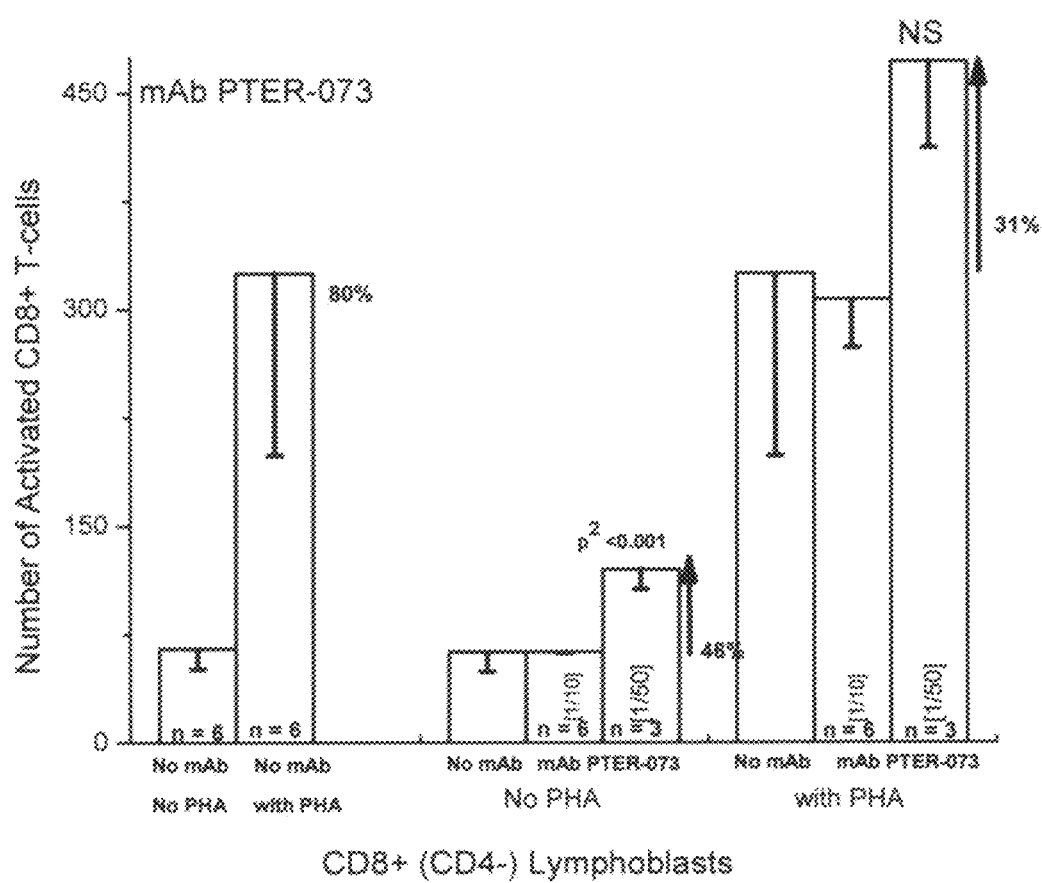
FIG. 8 shows the number of activated CD8+ T-lymphoblasts after exposure to monospecific HLA-E monoclonal antibody PTER-073 at two different concentrations or dilutions (1/10 & 1/50) in the presence or absence of PHA. Note that stimulation or activation of CD8+ T lymphocytes occur even without PHA suggesting the immunomodulatory potential of the exemplary HLA-E monospecific monoclonal antibody.
Figure 9:
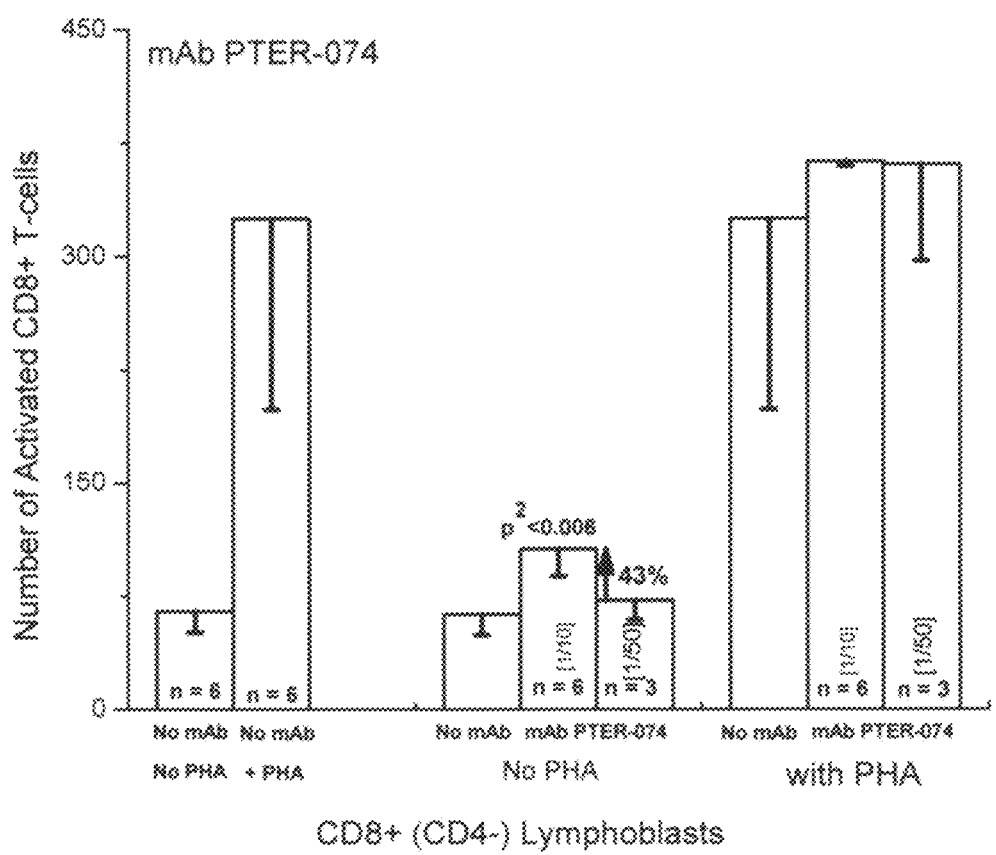
FIG. 9 shows the number of activated CD8+ T-lymphoblasts after exposure to monospecific HLA-E monoclonal antibody PTER-074 at two different concentrations or dilutions (1/10 & 1/50) in the presence or absence of PHA. Note that stimulation or activation of CD8+ T lymphocytes occur even without PHA suggesting the immunomodulatory potential of the exemplary monospecific HLA-E monoclonal antibody.
Figure 10:
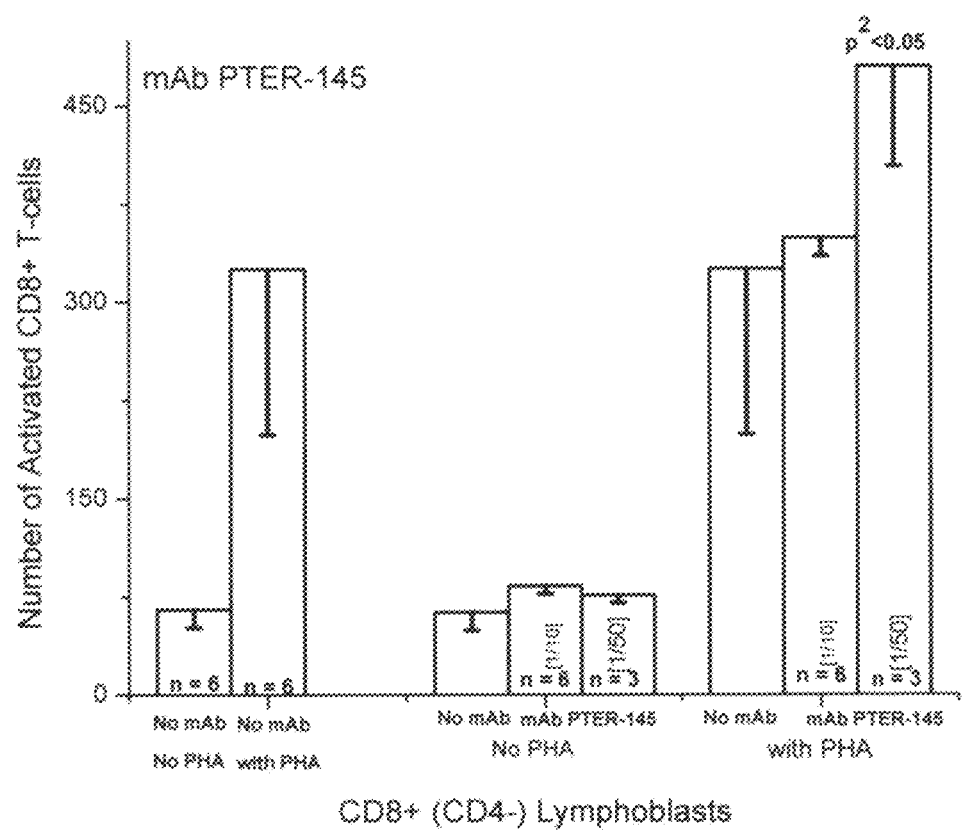
FIG. 10 shows the number of activated CD8+ T-lymphoblasts after exposure to monospecific HLA-E monoclonal antibody PTER-145 at two different concentrations or dilutions (1/10 & 1/50) in the presence or absence of PHA. Note that stimulation or activation of CD8+ T lymphocytes occur even without PHA suggesting the immunomodulatory potential of the exemplary monospecific HLA-E monoclonal antibody.
Figure 11:
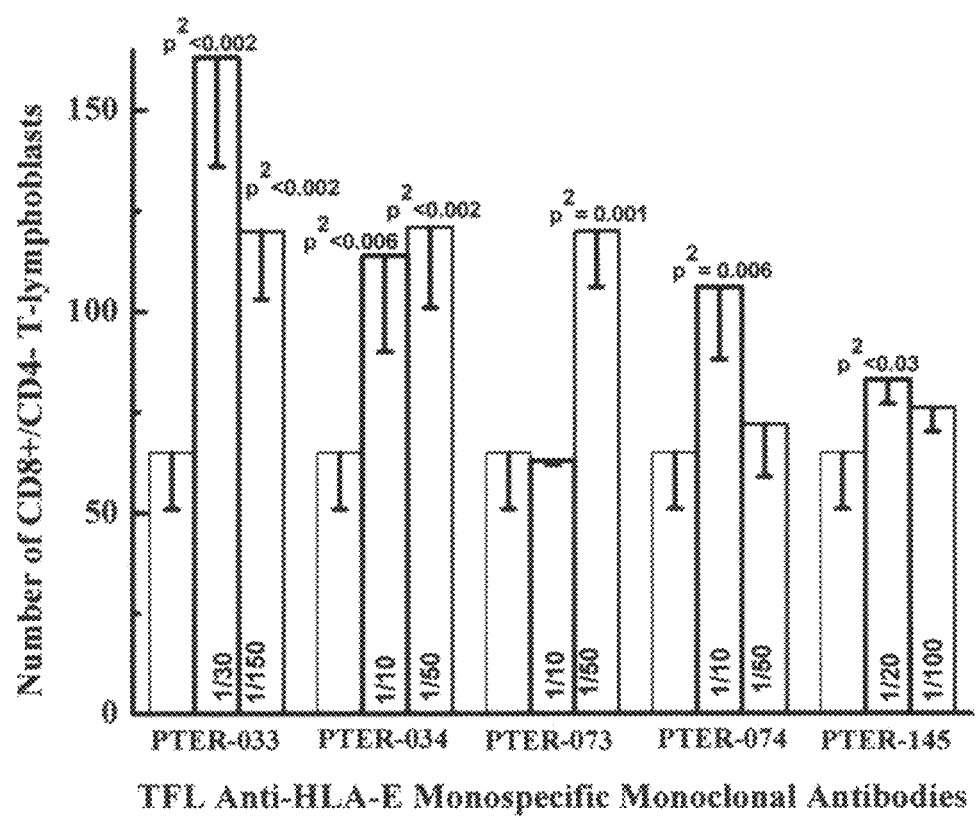

FIG. 11 shows comparison of CD8+ T-cell proliferative potential of different monospecific HLA-E monoclonal antibodies, PTER0033 (Rank #1), PTER0034 (Rank #2), PTER0073 (Rank #3, PTER0074 (Rank #4) & PTER0145 (Rank #5) at two different concentrations or dilutions (without PHA). Ranking is based on the statistical difference between mAb exposed and unexposed CD8+ T cells. Note that stimulation or activation of CD8+ T lymphocytes occur even without PHA suggesting the immunomodulatory potential of the exemplary monospecific HLA-E monoclonal antibody. Also note that mAb potentially useful for immunodiagnosis (PTER-0145) is not potential immunomodulator, whereas PTER-0033 is a potential generator of CD8+ T-lymphoblasts.

Both Table 4 and FIGS. 6 to 11 document that monospecific HLA-E monoclonal antibodies have the potential to induce blastogenesis and proliferation of CD8+ T lymphocytes specifically. The efficacy of non-specific anti-HLA-E mAb is much lower than that of monospecific HLA-E monoclonal antibodies. Hence, HLA-E monospecific monoclonal antibodies are potential therapeutic agents for augmenting the production of cytotoxic CD8+ T lymphocytes in patients with cancer patients.

As used herein, administering purified, humanized murine or human monoclonal anti-HLA-E monospecific monoclonal antibodies (as described herein) to cancer patients, preferably at any stage of cancer is referred to as "passive immunotherapy," a therapeutic procedure or protocol often used in FDA approved clinical trials on cancer patients. A two-fold objective can be achieved by passive immunotherapy with HLA-E monospecific monoclonal antibodies. First, the mAbs can neutralize cell surface or soluble HLA-E in circulation or in tumor microenvironment, which may otherwise bind to CD94/NKGa2 receptors and prevent CD8+ cytotoxic T cells (CTL) or NKT cells from attacking and killing tumor cells. Second, the anti-HLA-E monospecific antibodies bind to CD8+ cytotoxic T lymphocytes and promote their blastogenesis and proliferation such that the very high infiltrating CTL numbers nullify the negative the effect of HLA-E overexpressed on cancer cells.

Luminex® xMAP® multiplex technology, the single Ag (allele) assays were carried out for data acquisition and quantitative (Mean Florescent Intensity or MFI) estimation of the level of DR2 and DR4Abs. The Luminex® assays utilize microbeads on which individual DR2 and DR4 antigens have been covalently bonded (xMap® assays). XMap® microbeads contain two reporter fluorophores that are proportionally varied to identify them as one of 100 possible bead identifiers. The recombinant DR2 and DR4 antigens were attached to 5.6μ polystyrene microspheres by a process of simple chemical coupling, the microspheres internally dyed at One Lambda with red and infrared fluorophores, using different intensities of two dyes (xMAP® microsphere number #005).

Example 4

Therapeutic Relevance of the HLA-E-monospecific Monoclonal Antibodies: Augmenting the Production of Antibodies by Memory B Cells The immune system can memorize previously encountered antigens from pathogens and tumor cells during tumorigenesis by continued production of specific antibodies, i.e., the humoral memory. B cells can develop into two major types of memory cells, namely, memory B cells and memory plasma cells. Memory B cells do not constitutively express any effector function, requiring re-stimulation before they can contribute to the memory response. This form of memory is flexible, and can be regulated according to the amount of biologics or small molecules and the immune environment. In humans, memory B cells have been characterized by the faster and enhanced production of specific antibodies, isotype switching, and affinity maturation. Memory B cells may rarely be found in circulation or in blood but may be found in heterogeneous locations such as spleen (vaccina proteins), bone marrow or lymphoid tissues (Epstein-Barr virus). However memory B cells may found among peripheral blood lymphocytes in low number particularly when antibodies are in circulation. These memory B cells can be recovered by negative selection with magnetic beads.

Blood samples were collected from a healthy female after informed consent, and having high titer of antibodies for HLA class II alleles, DR-2 and DR-4. These antibodies were formed during her pregnancy when the child was positive for these alleles when the mother is negative. The blood samples were collected in heparinized tubes, pooled, and diluted in 1 vol of PBS (10 mM potassium/sodium phosphate buffer with 136 mM NaCl (pH). RBCs were removed by lysis with 0.83% (w/v) $NH_4Cl$ and platelets by a second centrifugation over Ficoll-Paque diluted 1/2 with PBS. B lymphocytes were purified by negative selection using the StemSep CD19 mixture according to the manufacturer's instructions (StemCell Technologies). Purified human B lymphocytes were 90% CD 19 as determined by flow cytometry analysis. Human B lymphocytes were cultured in IMDM supplemented with 10% heat-inactivated ultra-low IgG FBS (Life Technologies), 5 μg/ml bovine insulin, 5 μg/ml bovine transferrin, antibiotics, and 100 U/ml IL-4 and/or 25 U/ml IL-10 and/or 50 U/ml IL-2 and or anti-CD40 mAb or purified CD40L. Cell counts and viability were evaluated in triplicates by trypan blue exclusion using a hemacytometer. B lymphocytes were cultured for short-term (12 days). During these periods, cells were always about 95% for CD19+. Both sera of the female as well as the culture supernatants were monitored using microbeads coated with DR2 and DR4 antigens. Data generated with Luminex® Multiplex Flow Cytometry (LABScan® 100) were analyzed using computer software. PE-conjugated anti-Human IgG Abs were used for the immunolocalization of the Ab bound to Ags coated on to the microbeads. The reporter fluorophore intensity was then measured in a specialized flow cytometer together with the microbead identifiers, and the fluorescence measurement was classified by bead identifier. The Trimmed Mean was obtained by trimming a percent off the high and low ends of a distribution and finding the mean of the remaining distribution. The results are illustrated in FIG. 12.

Figure 12:
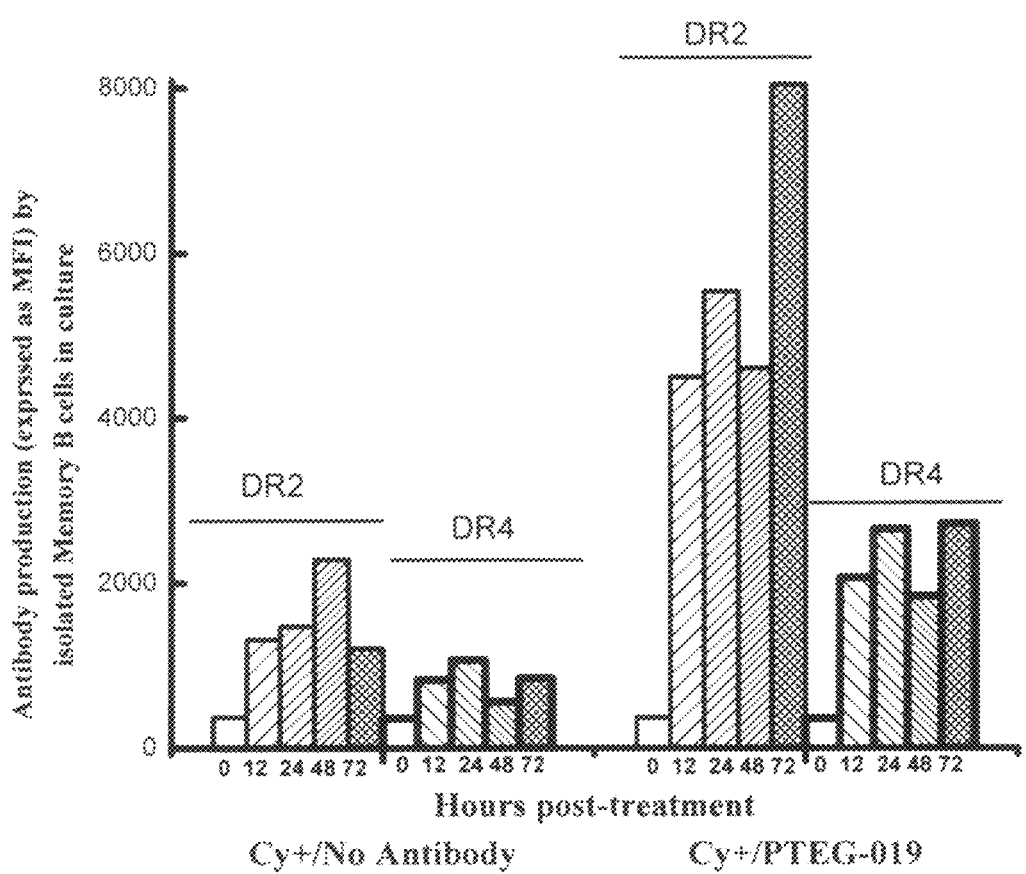

FIG. 12 illustrates the induction of IgG antibody production by memory B cells (CD19+/CD27+) isolated from normal healthy female expressing antibodies to HLA class II antigens, DR2 and DR4. Upon isolation the B cells were cultured in the presence of cytokines and CD40 ligand or anti-CD40 mAb. No HLA-E specific mAbs were added in control wells, whereas in the experimental well exemplary mAb PTEG-0019 was added after Protein G elution and concentration of the hybridoma culture supernatants. The antibody secreted by the memory B cells were recovered from culture chambers recovered at 0 hr, 12 hr, 24 hr, 48 hr and 72 hr and tested against microbeads coated with DR2 or DR4 using Luminex Flow cytometry. The values show that the anti-HLA-E monospecific mAb augmented the production of IgG antibodies against DR2 and Dr-4.

This example illustrates that HLA-E monospecific mAbs have the potential to augment antibody production by memory B cells. Increase in the number of memory B cells is expected in the wells with cytokines and CD40L, particularly on day 7 to 11. In wells without cytokines and CD40L no increase in number can be expected due to want of stimulation. However our analyses showed increased antibody production in both well upon addition of HLA-E monospecific monoclonal antibodies. The observations document induction of antibodies by memory B cells by HLA-E monospecific monoclonal antibody.

The ability of HLA-E monospecific monoclonal antibody to induce antibody production by memory B cells in circulation (of occur in low numbers) can be applied as a passive immunotherapy tool to augment antibodies against tumor associated antigens. Such antibodies can bind to tumor cells in tumor tissues or in circulation and elicit antibody dependent cytotoxicity (ADCC) or complement mediated cytotoxicity (CDC). If the antibodies produced against tumor antigens are multispecific there is a good chance of achieve tumor killing because some of the antibodies may even block complement restriction factors (CD46, CD55 and CD59) on tumor cells to promote CDC.

All the aforementioned examples illustrate that anti-HLA-E monospecific monoclonal antibodies serve as reliable and specific tool for immunodiagnosis of tumor cells overexpressing HLA-E. Clinically quantitation of immunodiagnosis would be beneficial for the density of HLA-E on tumor cell surface may have relevance to suppression of cytotoxic functions of CTLs or cytotoxic CD8+ T cells and NKT cells. In addition, HLA-E monospecific monoclonal antibodies act like a double-edged sword to serve as a passive immunotherapeutic agent. On one hand it can bind to cell surface or soluble HLA-E and block their ligand-receptor interaction with CD94/NKG2a so that it will suppress the cytotoxic functions of CD8+ T cells and NKT cells and on the other hand it can induce proliferation of activated CD8+ T lymphocytes and lymphoblasts. Increased number of CD8+ cells provides survival benefit for cancer patients (see, e.g. Gooden et al. 2011). Furthermore, HLA-E monospecific monoclonal antibodies can selectively augment to production antibodies against tumor associated antigens so that the anti-tumor antibodies can bring about ADCC and CDC. For passive immunotherapy, chimeric or humanized HLA-E monospecific antibodies either as antibodies or antibodies conjugated with co-stimulatory molecules, small molecules or drugs, would serve as potential therapeutic agents for treatment of cancer.

TABLE 1

Exemplary peptide sequences of HLA-E and their presence in HLA alleles.

| HLA-E peptide SEQ sequences ID [number of No: amino acids] | HLA alleles | | | | | Specificity |
|---|---|---|---|---|---|---|
| | Classical class Ia | | | Non-Classical class Ib | | |
| | A | B | Cw | F | G | |
| 1 $^{47}$PRAPWMEQE$^{55}$ [9] | 1 | 0 | 0 | 0 | 0 | A*3306 |
| 2 $^{59}$EYWDRETR$^{65}$ [8] | 5 | 0 | 0 | 0 | 0 | A restricted |
| 3 $^{65}$RSARDTA$^{71}$ [7] | 0 | 0 | 0 | 0 | 0 | E-restricted |
| 4 $^{90}$AGSHTLQW$^{97}$ [8] | 1 | 10 | 48 | 0 | 0 | Polyspecific |
| 5 $^{108}$RFLRGYE$^{123}$ [7] | 24 | 0 | 0 | 0 | 0 | A restricted |
| 6 $^{115}$QFAYDGKDY$^{123}$ [9] | 1 | 104 | 75 | 0 | 0 | Polyspecific |
| 7 $^{117}$AYDGKDY$^{123}$ [7] | 491 | 831 | 271 | 21 | 30 | Polyspecific |
| 8 $^{126}$LNEDLRSWTA$^{135}$ [10] | 239 | 219 | 261 | 21 | 30 | Polyspecific |
| 9 $^{137}$DTAAQI$^{142}$ [6] | 0 | 824 | 248 | 0 | 30 | Polyspecific |
| 10 $^{137}$DTAAQIS$^{143}$ [7] | 0 | 52 | 4 | 0 | 30 | Polyspecific |
| 11 $^{143}$SEQKSNDASE$^{152}$ [10] | 0 | 0 | 0 | 0 | 0 | E-restricted |
| 12 $^{157}$RAYLED$^{162}$ [6] | 0 | 1 | 0 | 0 | 0 | E& B*8201 restricted |

TABLE 1-continued

Exemplary peptide sequences of HLA-E and their presence in HLA alleles.

| HLA-E peptide SEQ sequences ID [number of No: amino acids] | HLA alleles | | | | | Specificity |
|---|---|---|---|---|---|---|
| | Classical class Ia | | | Non-Classical class Ib | | |
| | A | B | Cw | F | G | |
| 13 $^{163}$TCVEWL$^{168}$ [6] | 282 | 206 | 200 | 0 | 30 | Polyspecific |
| 14 $^{182}$EPPKTHVT$^{190}$ [8] | 0 | 0 | 19 | 0 | 0 | C restricted |

TABLE 2A

Peptide No. 1
PEPTIDE NO. 1 SPECIFIC FOR HLA-E

| HLA class I | a1 65 | a1 66 | a1 67 | a1 68 | a1 69 | a1 70 | a1 71 | a1 72 | a1 73 | SEQ ID NO: |
|---|---|---|---|---|---|---|---|---|---|---|
| E*01010 | R | S | A | R | D | T | A | Q | / | 15 |
| F*01010 | G | Y | A | K | A | N | A | Q | T | 16 |
| G*01010 | R | N | T | K | A | H | A | Q | T | 17 |
| A*allele | Highly variable and different from those of HLA-E | | | | | | | | | |
| B*allele | Highly variable and different from those of HLA-E | | | | | | | | | |
| C*allele | Highly variable and different from those of HLA-E | | | | | | | | | |

TABLE 2B

Peptide No. 2
PEPTIDE NO. 2 SPECIFIC FOR HLA-E

| HLA class I | Non-helical region | | | | | | | |
|---|---|---|---|---|---|---|---|---|
| | 102 | 103 | 104 | 105 | 106 | 107 | 108 | 109 |
| E*01010101 | E | L | G | P | D | R | R | F |
| F*01010101 | D | M | G | P | D | G | R | L |
| G*01010101 | D | L | G | S | D | G | R | L |
| A*allele | Highly variable and different from those of HLA-E | | | | | | | |
| B*allele | Highly variable and different from those of HLA-E | | | | | | | |
| C*allele | Highly variable and different from those of HLA-E | | | | | | | |

TABLE 2C

Peptide No. 3
PEPTIDE NO. 3 SPECIFIC FOR HLA-E

| HLA class I | a2 143 | a2 144 | a2 145 | a2 146 | a2 147 | a2 148 | a2 149 | a2 150 | a2 151 | a2 152 | a2 153 | a2 154 | a2 155 | a2 156 | a2 157 | a2 158 | a2 159 | a2 160 | a2 161 | a2 162 |
|---|---|---|---|---|---|---|---|---|---|---|---|---|---|---|---|---|---|---|---|---|
| E*01010101 | S | E | Q | K | S | N | D | A | S | E | A | E | H | Q | R | A | Y | L | E | D |
| F*01010101 | T | Q | R | F | Y | E | A | E | E | Y | A | E | E | F | R | T | Y | L | E | G |
| G*01010101 | S | K | R | K | C | E | A | A | N | V | A | E | Q | R | R | A | Y | L | E | G |
| A* allele | Highly variable and different from those of HLA-E | | | | | | | | | | | | | | | | | | | |
| B* allele | Highly variable and different from those of HLA-E | | | | | | | | | | | | | | | | | | | |
| C* allele | Highly variable and different from those of HLA-E | | | | | | | | | | | | | | | | | | | |

TABLE 2D

Peptide No. 4
Peptide No.4 Specific for HLA-E

| HLA class I | a2 170 | Non-helical region 171 | 172 | 173 | 174 | SEQ ID NO: |
|---|---|---|---|---|---|---|
| E*01010101 | K | Y | L | E | K | 24 |
| G*01010101 | R | Y | L | E | N | 25 |
| F*01010101 | R | Y | L | E | N | 25 |
| A*allele | Highly variable and different from those of HLA-E | | | | | |
| B*allele | Highly variable and different from those of HLA-E | | | | | |
| C*allele | Highly variable and different from those of HLA-E | | | | | |

TABLE 3

Exemplary Monospecific HLA-E Antibodies

| No. | Code for exemplary mAbs | Isotype | Mean Florescent Intensity of Undiluted culture supernatant of clones | | | | | |
|---|---|---|---|---|---|---|---|---|
| | | | HLA-E | HLA-F | HLA-G | HLA-A | HLA-B | HLA-Cw |
| 1 | PTER-109 | IgG2a | 23328 | <40 | <40 | <400 | <400 | <400 |
| 2 | PTEG-018 | IgG1 | 19227 | <40 | <40 | <400 | <400 | <400 |
| 3 | PTEG-019 | IgG1 | 19644 | <40 | <40 | <400 | <400 | <400 |
| 4 | PTEG-020 | IgG1 | 19075 | <40 | <150 | <400 | <400 | <400 |
| 5 | PTER-110 | IgG1 | 16226 | <40 | <40 | <400 | <400 | <400 |
| 6 | PTER-148 | IgG1 | 16644 | <40 | <40 | <400 | <400 | <400 |
| 7 | PTER-034 | IgG1 | 13272 | <40 | <60 | <400 | <400 | <400 |
| 8 | PTER-125 | IgG1 | 13204 | <40 | <40 | <400 | <400 | <400 |
| 9 | PTER-033 | IgG1 | 13025 | <40 | <60 | <400 | <400 | <400 |
| 10 | PTER-126 | IgG1 | 12397 | <40 | <40 | <400 | <400 | <400 |
| 11 | PTER-074 | IgG1 | 10269 | <40 | <40 | <400 | <400 | <400 |
| 12 | PTER-073 | IgG1 | 10088 | <40 | <40 | <400 | <400 | <400 |
| 13 | PTER-144 | IgG1 | 9180 | <40 | <40 | 0 | 0 | 0 |
| 14 | PTER-041 | IgG1 | 8914 | <40 | <40 | <400 | <400 | <400 |
| 15 | PTER-043 | IgG1 | 8448 | <40 | <40 | <400 | <400 | <400 |
| 16 | PTER-145 | IgG1 | 7622 | <40 | <40 | <400 | <400 | <400 |
| 17 | PTER-042 | IgG1 | 7452 | <40 | <40 | <400 | <400 | <400 |
| 18 | PTER-165 | IgG1 | 7280 | <40 | <40 | <400 | <400 | <400 |
| 19 | PTER-001 | IgG2a | 4691 | <40 | <40 | <400 | <400 | <400 |
| 20 | PTER-056 | IgG2a | 4581 | <40 | <40 | <400 | <400 | <400 |
| 21 | PTER-081 | IgG1 | 4261 | <40 | <40 | <400 | <400 | <400 |
| 22 | PTEG-088 | IgG1 | 1604 | <40 | <40 | <400 | <400 | <400 |
| 23 | PTER-016 | IgG2a | 1349 | <150 | <150 | <400 | <400 | <400 |
| 24 | PTER-047 | IgG1 | 1044 | <40 | <40 | <400 | <400 | <400 |

*Only monospecific HLA-E monoclonal antibodies are listed here, among the 258 mAbs developed, 24 showed monospecificity.

TABLE 4

| | | CD3+LYMPHOBLASTS | | | | | | | | | | CD3+NAIVE T-CELLS | | | |
|---|---|---|---|---|---|---|---|---|---|---|---|---|---|---|---|
| | | No PHA | | | | | With PHA | | | | | No PHA | | With PHA | |
| Dilutions | | CD4+/CD8- | CD4-/CD8+ | CD4+/CD8+ | CD4-/CD8- | Total | CD4+/CD8- | CD4+/CD8+ | CD4-/CD8- | Total | | CD4+/CD8- | CD4-/CD8+ | CD4+/CD8+ | CD4-/CD8- |
| | | No. mAb [N = 5] | | | | | | | | | | No. mAb [N = 5] | | | |
| 1/30 | Mean | 197 | 65 | 141 | 52 | 454 | 857 | 325 | 128 | 239 | 1609 | 3063 | 547 | 1249 | 475 |
| | SD | 33 | 14 | 35 | 15 | 70 | 115 | 126 | 43 | 84 | 267 | 149 | 85 | 99 | 37 |
| | 2-tail p [<] | NS | 0.015 | NS | 0.005 | NS | 0.001 | 0.001 | NS | 0.001 | 0.001 | NS | NS | <0.0001 | NS |
| | | mAb-PTER-033 [N = 3] | | | | | | | | | | | | | |
| 1/30 | Mean | 223 | 163 | 153 | 99 | 414 | 1129 | 505 | 152 | 412 | 2197 | 3185 | 755 | 1170 | 535 |
| | SD | 40 | 27 | 80 | 13 | 120 | 86 | 23 | 16 | 20 | 139 | 180 | 145 | 58 | 12 |
| | 2-tail p [<] | NS | 0.015 | NS | 0.005 | NS | 0.010 | 0.016 | NS | 0.014 | 0.004 | NS | NS | NS | 0.009 |
| 1/150 | Mean | 252 | 120 | 205 | 68 | 645 | 1266 | 572 | 157 | 412 | 2407 | 3238 | 681 | 1149 | 508 |
| | SD | 30 | 17 | 13 | 9 | 28 | 80 | 31 | 14 | 16 | 116 | 14 | 64 | 21 | 22 |
| | 2-tail p [<] | 0.047 | 0.001 | 0.020 | NS | 0.003 | 0.001 | 0.003 | NS | 0.001 | 0.001 | NS | NS | NS | NS |
| | | mAb-PTER-034 [N = 3] | | | | | | | | | | | | | |
| 1/10 | Mean | 213 | 114 | 182 | 71 | 580 | 801 | 322 | 117 | 207 | 1446 | 3048 | 631 | 1140 | 487 |
| | SD | 16 | 24 | 10 | 22 | 44 | 97 | 29 | 2 | 36 | 162 | 83 | 90 | 158 | 54 |
| | 2-tail p [<] | NS | 0.005 | 0.034 | NS | 0.015 | NS | NS | NS | NS | NS | NS | NS | NS | NS |
| 1/50 | Mean | 229 | 121 | 186 | 104 | 640 | 1424 | 600 | 160 | 362 | 2547 | 3354 | 687 | 1098 | 445 |
| | SD | 35 | 20 | 14 | 14 | 45 | 142 | 39 | 9 | 24 | 197 | 132 | 26 | 26 | 17 |
| | 2-tail p [<] | NS | 0.002 | 0.027 | 0.005 | 0.003 | 0.007 | 0.009 | NS | 0.009 | 0.001 | NS | 0.009 | 0.012 | NS |
| | | mAb-PTER-073 | | | | | | | | | | | | | |
| 1/10 | Mean | 153 | 63 | 137 | 58 | 411 | 662 | 307 | 107 | 209 | 1285 | 2850 | 440 | 1089 | 374 |
| | SD | 23 | 1 | 15 | 19 | 14 | 78 | 33 | 8 | 40 | 152 | 92 | 14 | 132 | 36 |
| | 2-tail p [<] | NS | NS | NS | NS | NS | NS | NS | NS | NS | NS | NS | NS | NS | 0.030 |
| 1/50 | Mean | 233 | 120 | 208 | 82 | 643 | 1009 | 472 | 140 | 425 | 2045 | 3119 | 637 | 1053 | 437 |
| | SD | 25 | 14 | 24 | 15 | 47 | 106 | 60 | 16 | 119 | 287 | 72 | 53 | 80 | 49 |
| | 2-tail p [<] | NS | 0.001 | 0.02 | 0.03 | 0.004 | NS | NS | NS | NS | NS | NS | NS | 0.021 | NS |
| | | mAb-PTER-074 [N = 3] | | | | | | | | | | | | | |
| 1/10 | Mean | 214 | 106 | 201 | 66 | 587 | 840 | 353 | 141 | 278 | 1623 | 2933 | 362 | 1252 | 515 |
| | SD | 13 | 18 | 18 | 9 | 25 | 119 | 3 | 20 | 56 | 179 | 95 | 304 | 75 | 51 |
| | 2-tail p [<] | NS | 0.006 | 0.029 | NS | 0.017 | NS | NS | NS | NS | NS | NS | NS | NS | NS |
| 1/50 | Mean | 178 | 72 | 130 | 55 | 435 | 751 | 361 | 74 | 257 | 1444 | 3401 | 624 | 1193 | 521 |
| | SD | 27 | 13 | 15 | 3 | 40 | 154 | 64 | 19 | 52 | 273 | 28 | 13 | 8 | 17 |
| | 2-tail p [<] | NS | NS | NS | NS | NS | NS | NS | NS | NS | NS | 0.007 | NS | NS | NS |
| | | mAb-PTER-145 [N = 3] | | | | | | | | | | | | | |

TABLE 4-continued

| | | CD3+LYMPHOBLASTS | | | | | | | | CD3+NAIVE T-CELLS | | | | | |
|---|---|---|---|---|---|---|---|---|---|---|---|---|---|---|---|
| | | No PHA | | | | With PHA | | | | No PHA | | With PHA | | | |
| | | No. mAb [N = 5] | | | | | | | | | No. mAb [N = 5] | | | | |
| Dilutions | | CD4+/CD8− | CD4−/CD8+ | CD4+/CD8+ | CD4−/CD8− | Total | CD4+/CD8− | CD4−/CD8+ | CD4+/CD8+ | CD4−/CD8− | Total | CD4+/CD8− | CD4−/CD8+ | CD4+/CD8− | CD4−/CD8+ | CD4−/CD8− |
| 1/20 | Mean | 173 | 83 | 157 | 47 | 459 | 771 | 349 | 97 | 257 | 1474 | 3349 | 728 | 1206 | 500 | |
| | SD | 18 | 6 | 27 | 2 | 43 | 61 | 14 | 6 | 49 | 35 | 169 | 50 | 58 | 85 | |
| | 2-tailp | NS | NS | NS | NS | NS | NS | NS | NS | NS | NS | NS | 0.006 | NS | 0.67 | |
| 1/100 | Mean | 238 | 76 | 168 | 66 | 548 | 1118 | 480 | 118 | 282 | 1998 | 3200 | 537 | 1160 | 41.0 | |
| | SD | 32 | 6 | 9 | 9 | 12 | 65 | 71 | 23 | 74 | 221 | 229 | 37 | 14 | 30 | |
| | 2-tail p | NS | NS | NS | NS | 0.02 | 0.005 | 0.05 | NS | NS | NS | NS | NS | NS | 0.033 | |
| | | | | | | | mAb-PTER-007 (HLA-E non-specific) [N = 3] | | | | | | | | | |
| 1/10 | Mean | 164 | 63 | 145 | 52 | 424 | 676 | 317 | 100 | 222 | 1315 | 2876 | 451 | 1183 | 444 | |
| | SD | 33 | 2 | 3 | 17 | 47 | 79 | 25 | 4 | 29 | 125 | 136 | 72 | 19 | 26 | |
| | 2-tail p | NS | NS | NS | NS | NS | 0.027 | NS | NS | NS | NS | NS | NS | NS | NS | |
| 1/50 | Mean | 230 | 107 | 193 | 80 | 610 | 892 | 443 | 122 | 339 | 1795 | 3088 | 667 | 1075 | 491 | |
| | SD | 23 | 7 | 17 | 4 | 26 | 26 | 18 | 8 | 21 | 38 | 65 | 16 | 55 | 48 | |
| | 2-tail p | NS | 0.005 | 0.019 | 0.006 | 0.002 | NS | NS | NS | NS | NS | NS | 0.018 | 0.013 | NS | |

What is claimed:

1. An antibody comprising the heavy chain and light chain complementarity determining regions of the antibody that is produced by the hybridoma that is deposited at American Type Culture Collection Patent Deposit Number PTA-125908.

2. The antibody of claim 1 that is produced by the hybridoma that is deposited at American Type Culture Collection Patent Deposit Number PTA-125908.

3. A pharmaceutical composition comprising the antibody of claim 1 and one or more pharmaceutically acceptable carriers.

4. The composition of claim 1, wherein the composition is suitable for subcutaneous, intravenous, or intramuscular administrations.

5. A pharmaceutical composition comprising the antibody of claim 2 and one or more pharmaceutically acceptable carriers.

6. The composition of claim 5, wherein the composition is suitable for subcutaneous, intravenous, or intramuscular administrations.

7. The antibody of claim 1 that provides specific binding to HLA-E relative to other HLA antigens.

* * * * *

SEQUENCE LISTING

<160> NUMBER OF SEQ ID NOS: 28

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide

<400> SEQUENCE: 1

Pro Arg Ala Pro Trp Met Glu Gln Glu
1               5

<210> SEQ ID NO 2
<211> LENGTH: 8
<212> TYPE: PRT
<213> ORGANISM: Artificial Sequence
<220> FEATURE:
<223> OTHER INFORMATION: Synthetic peptide

<400> SEQUENCE: 2

Glu Tyr Trp Asp Arg Glu Thr Arg
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Ala Gly Ser His Thr Leu Gln Trp
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic peptide

<400> SEQUENCE: 4

Arg Phe Leu Arg Gly Tyr Glu
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic peptide

<400> SEQUENCE: 5

Gln Phe Ala Tyr Asp Gly Lys Asp Tyr
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic peptide

<400> SEQUENCE: 6

Ala Tyr Asp Gly Lys Asp Tyr
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic peptide

<400> SEQUENCE: 7

Leu Asn Glu Asp Leu Arg Ser Trp Thr Ala
1               5                   10

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Asp Thr Ala Ala Gln Ile
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic peptide

<400> SEQUENCE: 9

Asp Thr Ala Ala Gln Ile Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Arg Ala Tyr Leu Glu Asp
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Thr Cys Val Glu Trp Leu
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Glu Pro Pro Lys Thr His Val Thr
1               5

```
<210> SEQ ID NO 13
<211> LENGTH: 7
<212> TYPE: PRT
<213> ORGANISM: Artificial Sequence
<220> FEATURE:
<223> OTHER INFORMATION: Synthetic peptide

<400> SEQUENCE: 13

Arg Ser Ala Arg Asp Thr Ala
1               5

<210> SEQ ID NO 14
<211> LENGTH: 10
<212> TYPE: PRT
<213> ORGANISM: Artificial Sequence
<220> FEATURE:
<223> OTHER INFORMATION: Synthetic peptide

<400> SEQUENCE: 14

Ser Glu Gln Lys Ser Asn Asp Ala Ser Glu
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic peptide

<400> SEQUENCE: 15

Arg Ser Ala Arg Asp Thr Ala Gln Ile
1               5

<210> SEQ ID NO 16
<211> LENGTH: 9
<212> TYPE: PRT
<213> ORGANISM: Artificial Sequence
<220> FEATURE:
<223> OTHER INFORMATION: Synthetic peptide

<400> SEQUENCE: 16

Gly Tyr Ala Lys Ala Asn Ala Gln Thr
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic peptide

<400> SEQUENCE: 17

Arg Asn Thr Lys Ala His Ala Gln Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Glu Leu Gly Pro Asp Arg Arg Phe
1               5
```

```
<210> SEQ ID NO 19
<211> LENGTH: 8
<212> TYPE: PRT
<213> ORGANISM: Artificial Sequence
<220> FEATURE:
<223> OTHER INFORMATION: Synthetic peptide

<400> SEQUENCE: 19

Asp Met Gly Pro Asp Gly Arg Leu
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

<400> SEQUENCE: 20

Asp Leu Gly Ser Asp Gly Arg Leu
1               5

<210> SEQ ID NO 21
<211> LENGTH: 20
<212> TYPE: PRT
<213> ORGANISM: Artificial Sequence
<220> FEATURE:
<223> OTHER INFORMATION: Synthetic peptide

<400> SEQUENCE: 21

Ser Glu Gly Lys Ser Asn Asp Ala Ser Glu Ala Glu His Gln Arg Ala
1               5                   10                  15

Tyr Leu Glu Asp
            20

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide

<400> SEQUENCE: 22

Thr Gln Arg Phe Tyr Glu Ala Glu Glu Tyr Ala Glu Glu Phe Arg Thr
1               5                   10                  15

Tyr Leu Glu Gly
            20

<210> SEQ ID NO 23
<211> LENGTH: 20
<212> TYPE: PRT
<213> ORGANISM: Artificial Sequence
<220> FEATURE:
<223> OTHER INFORMATION: Synthetic peptide

<400> SEQUENCE: 23

Ser Lys Arg Lys Cys Glu Ala Ala Asn Val Ala Glu Gln Arg Arg Ala
1               5                   10                  15

Tyr Leu Glu Gly
            20

<210> SEQ ID NO 24
<211> LENGTH: 5
<212> TYPE: PRT
<213> ORGANISM: Artificial Sequence
<220> FEATURE:
```

```
<223> OTHER INFORMATION: Synthetic peptide

<400> SEQUENCE: 24

Lys Tyr Leu Glu Lys
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic peptide

<400> SEQUENCE: 25

Arg Tyr Leu Glu Asn
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic peptide

<400> SEQUENCE: 26

Arg Asp Gln Ile Arg Val Arg
1               5

<210> SEQ ID NO 27
<211> LENGTH: 9
<212> TYPE: PRT
<213> ORGANISM: Artificial Sequence
<220> FEATURE:
<223> OTHER INFORMATION: Synthetic peptide

<400> SEQUENCE: 27

Val Met Ala Pro Arg Thr Leu Phe Leu
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide

<400> SEQUENCE: 28

Glu Asp Ala His Glu Ser
1               5
```